(12) United States Patent
Takeda

(10) Patent No.: US 12,352,694 B2
(45) Date of Patent: Jul. 8, 2025

(54) DETECTION DEVICE AND DETECTION METHOD

(71) Applicant: Panasonic Intellectual Property Management Co., Ltd., Osaka (JP)

(72) Inventor: Eiji Takeda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 857 days.

(21) Appl. No.: 17/523,583

(22) Filed: Nov. 10, 2021

(65) Prior Publication Data
US 2022/0065784 A1 Mar. 3, 2022

Related U.S. Application Data

(63) Continuation of application No. PCT/JP2020/023438, filed on Jun. 15, 2020.

(30) Foreign Application Priority Data

Jul. 3, 2019 (JP) ................. 2019-124407

(51) Int. Cl.
*G01N 21/64* (2006.01)
*G01N 33/569* (2006.01)

(52) U.S. Cl.
CPC ....... *G01N 21/648* (2013.01); *G01N 21/6408* (2013.01); *G01N 33/56983* (2013.01)

(58) Field of Classification Search
CPC ............. G01N 21/648; G01N 21/6408; G01N 33/56983; G01N 2021/6439; G01N 33/582; G01N 21/01; G01N 21/6402
See application file for complete search history.

(56) References Cited

U.S. PATENT DOCUMENTS

2006/0270919 A1  11/2006  Brenner
2008/0014581 A1  1/2008  Nakahara et al.
(Continued)

FOREIGN PATENT DOCUMENTS

JP  2007-171158  7/2007
JP  2008-216046  9/2008
(Continued)

OTHER PUBLICATIONS

International Search Report of PCT application No. PCT/JP2020/023438 dated Aug. 25, 2020.

*Primary Examiner* — Jennifer Wecker
*Assistant Examiner* — Britney N. Washington
(74) *Attorney, Agent, or Firm* — Wenderoth, Lind & Ponack, L.L.P.

(57) ABSTRACT

A detection device is for detecting a detection target substance using a metal material modified with a first substance having a property of specifically binding to the detection target substance and a fluorescent material modified with a second substance having a property of specifically binding to the detection target substance. The detection device includes: a light source configured to emit light for exciting the fluorescent material; a photodetector configured to detect fluorescence emitted by the fluorescent material over time for a specific period from when emission of the light by the light source is stopped; and a processor configured to detect the detection target substance in a complex formed of the metal material, the detection target substance, and the fluorescent material binding to each other.

10 Claims, 10 Drawing Sheets

(56) References Cited

U.S. PATENT DOCUMENTS

| | | | |
|---|---|---|---|
| 2008/0219893 A1* | 9/2008 | Ohtsuka | G01N 21/648 |
| | | | 422/82.08 |
| 2011/0025315 A1 | 2/2011 | Ohtsuka | |
| 2014/0256593 A1* | 9/2014 | Szmacinski | G01N 33/553 |
| | | | 435/7.1 |
| 2020/0319106 A1 | 10/2020 | Sasaki et al. | |

FOREIGN PATENT DOCUMENTS

| | | |
|---|---|---|
| JP | 2011-033454 | 2/2011 |
| JP | 2019-012041 | 1/2019 |
| WO | 2019/187910 | 10/2019 |

* cited by examiner

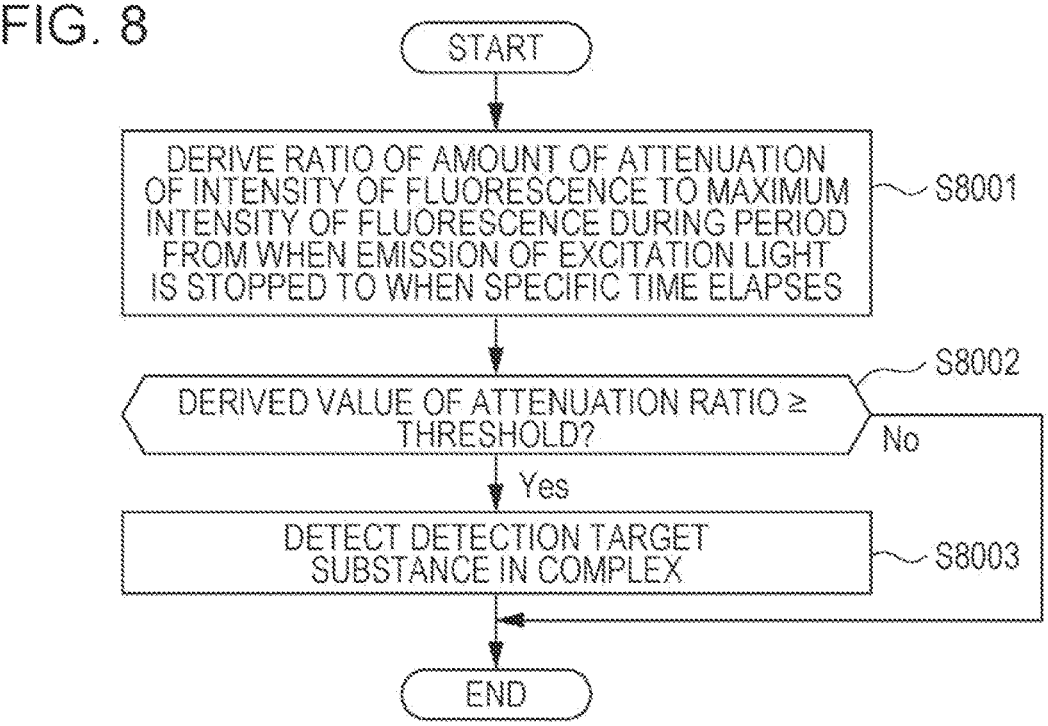
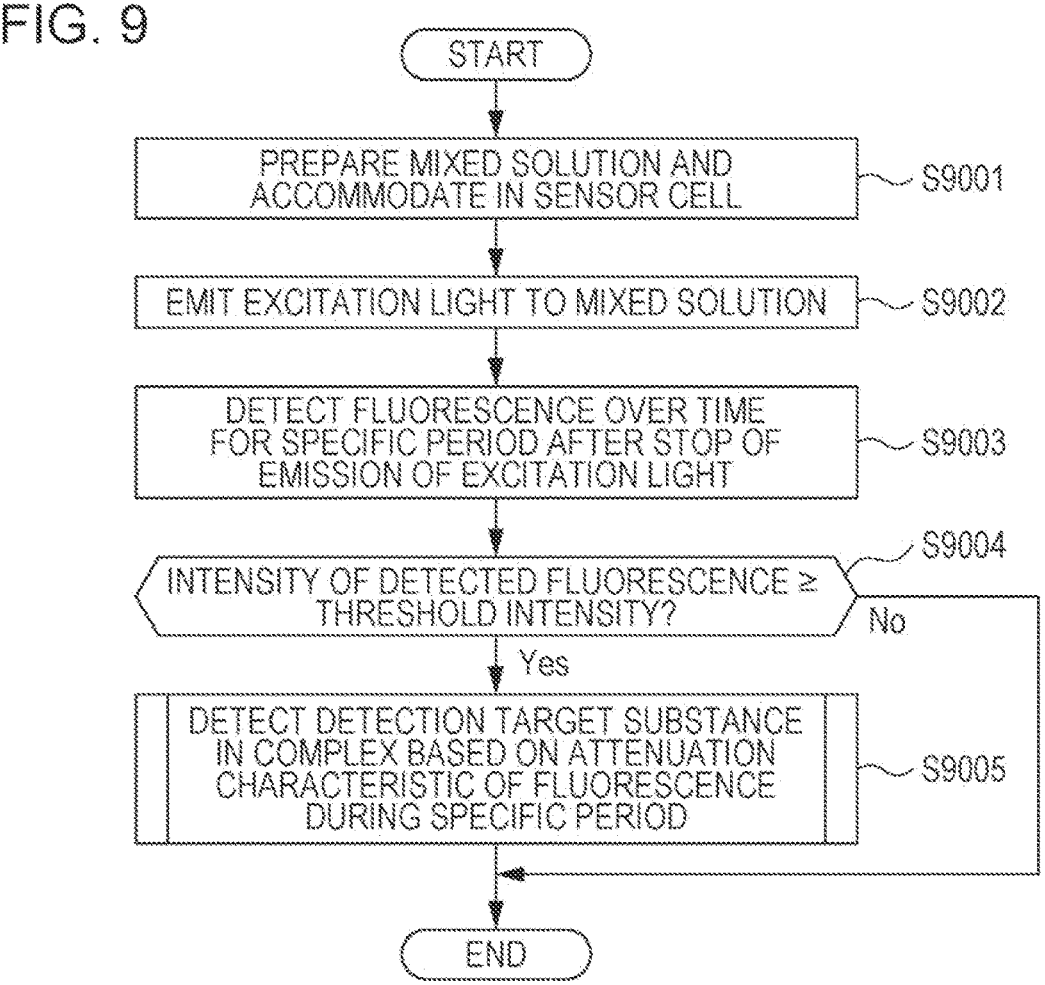

FIG. 12
(a)
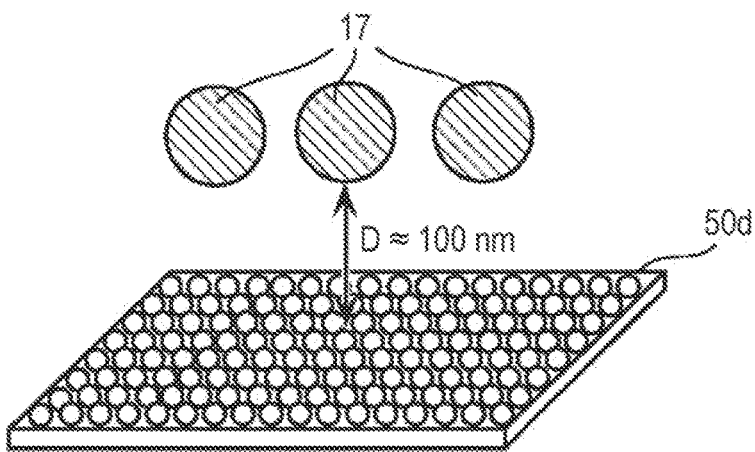
(b)
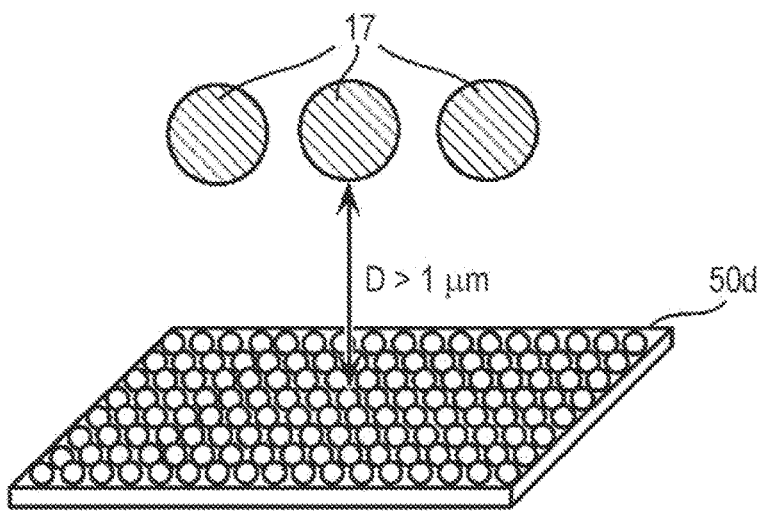
(c)
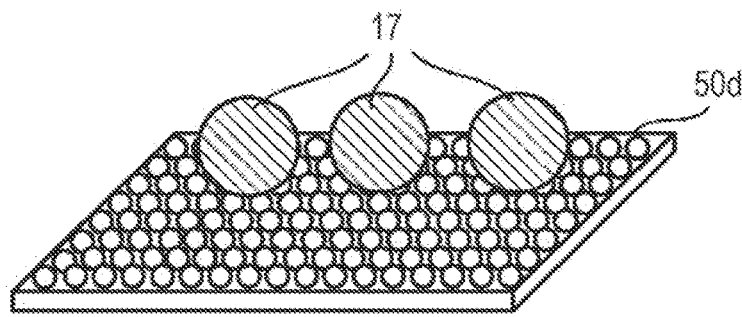

DETECTION DEVICE AND DETECTION METHOD

BACKGROUND

1. Technical Field

The present disclosure relates to a detection device and a detection method for detecting a detection target substance in a sample.

2. Description of the Related Art

As an existing well-known technique for detecting a detection target substance in a sample, a surface enhanced fluorescence method in which fluorescence is enhanced by the effect of localized surface plasmon resonance of metal microparticles is available. For example, Japanese Unexamined Patent Application Publication No. 2008-216046 discloses a technique in which a detection antibody to which a metal microparticle and a fluorescent material are joined is used, and fluorescence emitted from the fluorescent material is enhanced by plasmon resonance by the metal microparticle to thereby enable highly sensitive detection of a very small amount of detection target substance.

SUMMARY

However, with the existing technique described in Japanese Unexamined Patent Application Publication No. 2008-216046, it is not possible to distinguishably detect fluorescent enhanced due to variation in the particle size of the fluorescent material, aggregation, and the detection position and fluorescent enhanced by the effect of localized surface plasmon resonance. Therefore, it is difficult to consider that the existing technique described in Japanese Unexamined Patent Application Publication No. 2008-216046 enables highly accurate detection of a detection target substance in a sample.

One non-limiting and exemplary embodiment provides a detection device and a detection method that enable highly accurate detection of a detection target substance in a sample.

In one general aspect, the techniques disclosed here feature a detection device for detecting a detection target substance by using a metal material modified with a first substance having a property of specifically binding to the detection target substance and a fluorescent material modified with a second substance having a property of specifically binding to the detection target substance, the detection device including: a light source that emits light for exciting the fluorescent material; a photodetector that detects fluorescence emitted by the fluorescent material over time for a specific period from when emission of the light by the light source is stopped; and a processor that detects the detection target substance in a complex formed of the metal material, the detection target substance, and the fluorescent material binding to each other, on the basis of an attenuation characteristic of the fluorescence during the specific period.

According to the present disclosure, it is possible to detect a detection target substance in a sample with high accuracy.

It should be noted that this general or specific aspect may be implemented as a system, a method, an integrated circuit, a computer program, or a computer-readable recording medium or may be implemented as a combination of any of an apparatus, a system, a method, an integrated circuit, a computer program, and a recording medium. Examples of a computer-readable recording medium include a non-volatile recording medium such as a CD-ROM (compact disc readonly memory).

Additional benefits and advantages of the aspect of the present disclosure will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is a flowchart illustrating another example detailed process flow in the step in FIG. 6;

FIG. 9 is a flowchart illustrating another example operation of the detection device according to the first embodiment;

FIG. 12 includes diagrams schematically illustrating a positional relationship between a metal material and a fluorescent material in a first example, that in a first comparative example, and that in a second comparative example;

DETAILED DESCRIPTION

Underlying Knowledge Forming Basis of the Present Disclosure

As a technique for detecting a very small amount of detection target substance in a sample, a fluorescence method is commonly used. In this fluorescence method, a detection target substance is labeled with a fluorescent substance (hereinafter referred to as a fluorescent material), excitation light is applied to the fluorescent material, and fluorescence generated at this time is detected to thereby detect the detection target substance.

To increase the detection sensitivity of the fluorescence method described above, for example, a method using Surface Plasmon field-enhanced Fluorescence Spectroscopy (SPFS), that is, a surface enhanced fluorescence method, is available. In this method, a fluorescent substance is excited by surface plasmon resonance light generated by Surface Plasmon Resonance (SPR) to generate fluorescence, and the fluorescence, which is surface-plasmon-excited enhanced fluorescence (hereinafter referred to as surface enhanced fluorescence), is detected to thereby detect the detection target substance. In the surface enhanced fluorescence method, an intensity that is single- to triple-digit higher than that in usual fluorescence methods is observed, and therefore, a detection target substance in low concentration that is unable to be detected with usual fluorescence methods can be detected.

Although the surface enhanced fluorescence method is a fluorescence detection method having sensitivity higher than that of usual fluorescence methods, the surface enhanced fluorescence method is unable to distinguishably detect fluorescent enhanced due to variation in the particle size of the fluorescent material, aggregation, and the detection position and fluorescent enhanced by the effect of localized surface plasmon resonance.

Figure 1A:
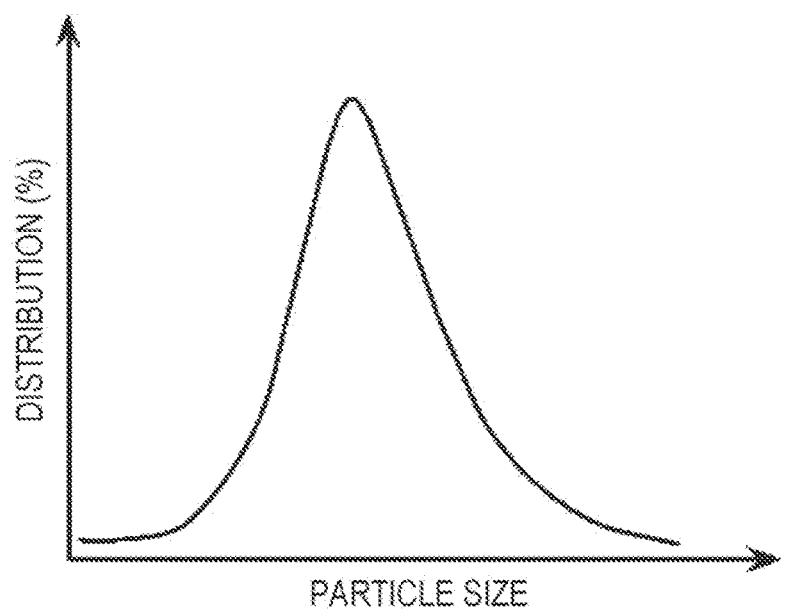
FIG. 1A is a diagram illustrating a relationship between the particle size of a fluorescent material and its distribution percentage.

FIG. 1A is a diagram illustrating a relationship between the particle size of a fluorescent material and its distribution percentage.

The particle size of not only a fluorescent material but also a particulate substance is always distributed within a specific range. This particle size distribution includes not only the particle size of a single particle of the particulate substance but also the particle size of an aggregate formed of aggregated particles of the particulate substance.

Figure 1B:
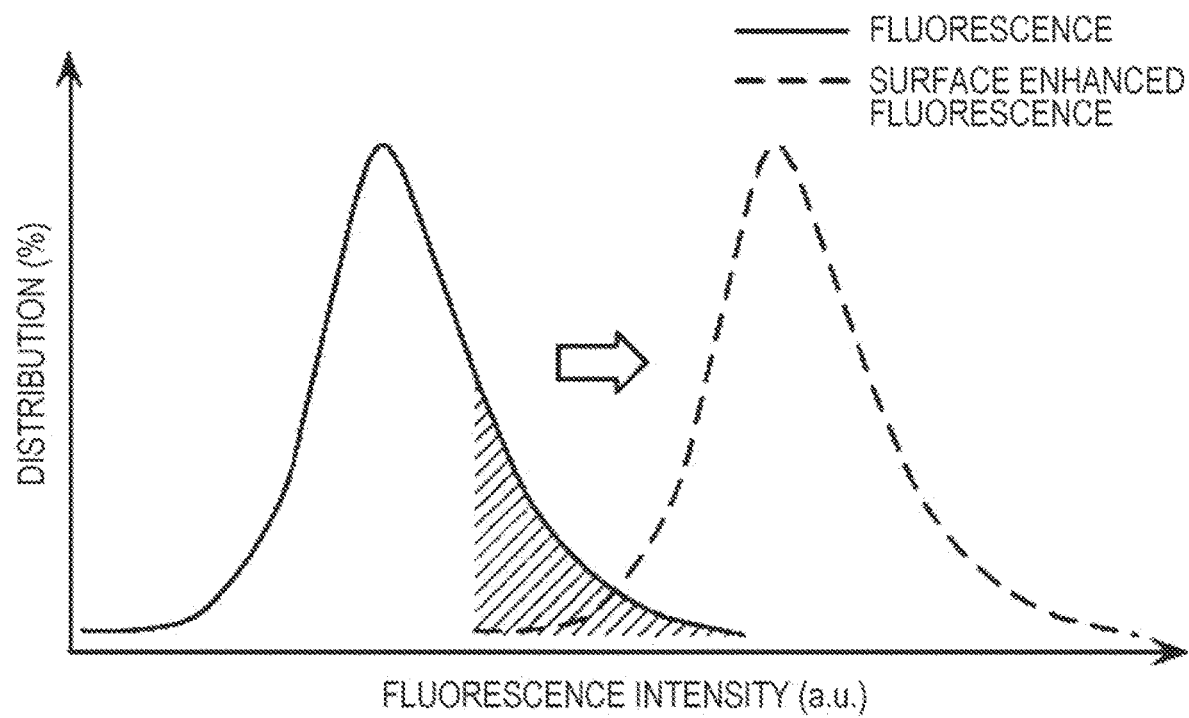
FIG. 1B is a diagram regarding the fluorescent material having the particle size distribution illustrated in FIG. 1A and illustrates a relationship between the intensity of fluorescence of the fluorescent material and its distribution percentage and a relationship between the intensity of surface enhanced fluorescence and its distribution percentage.

As illustrated in FIG. 1A, the particle size of a fluorescent material is distributed within a specific range. In general, as the particle size of a fluorescent material increases, the intensity of fluorescence emitted by the fluorescent material increases. Therefore, regarding the fluorescent material having the particle size distribution illustrated in FIG. 1A, a relationship between the intensity of fluorescence emitted by the fluorescent material and its distribution percentage is indicated by the solid line in FIG. 1B. When fluorescence of the fluorescent material having such a distribution is enhanced by localized surface plasmon resonance, the fluorescence intensity shifts in a direction in which the fluorescence intensity increases, as indicated by the dashed line in FIG. 1B. At this time, there is a part in which the intensity of fluorescence before enhancement and the intensity of fluorescence after enhancement overlap (the shaded part in FIG. 1B). Therefore, it is not possible to detect fluorescence emitted by a particle of the fluorescent material having a large particle size or an aggregate of particles of the fluorescent material corresponding to the overlap part, so as to be distinguishable from surface enhanced fluorescence.

Figure 2:
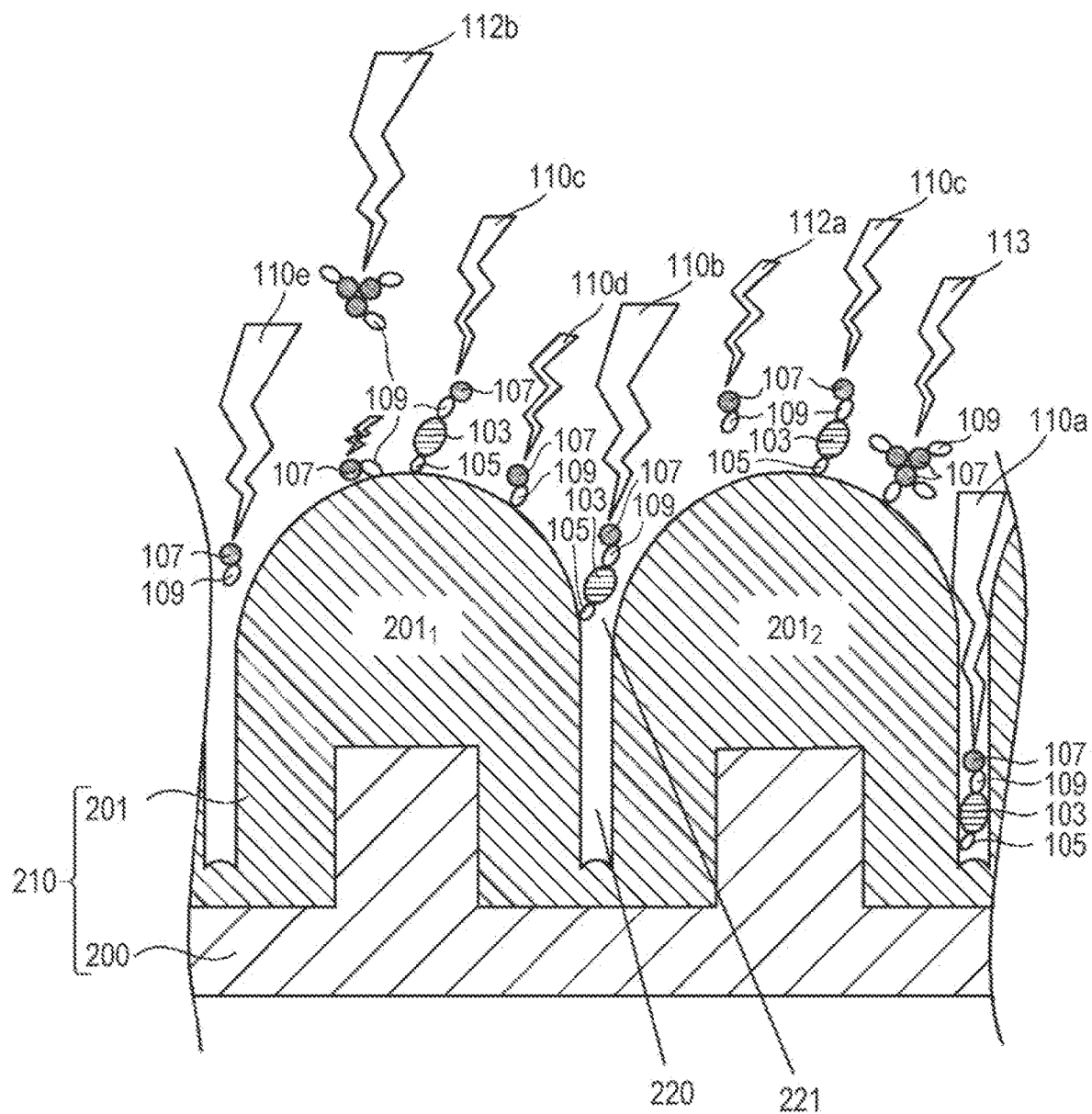
FIG. 2 is a diagram schematically illustrating a phenomenon that can occur in a surface enhanced fluorescence method.

FIG. 2 is a diagram schematically illustrating a phenomenon that can occur in the surface enhanced fluorescence method. FIG. 2 illustrates an example of using a plasmonic substrate 210 having a metal microstructure formed of a base material 200 and metal micro protrusions 201 disposed on the base material 200 at regular intervals. In FIG. 2, a metal micro protrusion 2011 and a metal micro protrusion 2012 are adjacent to each other.

In localized surface plasmon resonance, free electrons on the surface of the metal micro protrusions 201 having a microstructure in a size smaller than the wavelength of applied light are in resonance with the electromagnetic field of the applied light and oscillate, and a locally very strong electric field, that is, a locally enhanced electric field, is generated. This locally enhanced electric field is reduced sharply in a part away from the metal surface. As illustrated in FIG. 2, in a case where the metal micro protrusion 2011 and the metal micro protrusion 2012 are adjacent to each other, the strongest electric field is generated in a gap 220 between the metal micro protrusion 2011 and the metal micro protrusion 2012 adjacent to each other, and the electric field is larger as the width of the gap 220 is narrower. That is, the electric field intensity increases from a part in the vicinity of the gap between the metal micro protrusions 201 (an opening 221 of the gap) toward the gap, and the electric field intensity is smaller on the top side (the convex part) than in the opening of the gap between the metal micro protrusions 201.

FIG. 2 further illustrates a first substance 105 that is immobilized on the surface of the metal micro protrusion 201 and has the property of specifically binding to a detection target substance 103, the detection target substance 103, and a second substance 109 that is labeled with a fluorescent material 107 and has the property of specifically binding to the detection target substance 103. Here, localized surface plasmon resonance is used to detect a complex formed of the first substance 105 immobilized on the metal micro protrusion 201, the detection target substance 103, and the second substance 109 labeled with the fluorescent material 107 that are in sandwich binding.

As described above, the intensity of the locally enhanced electric field caused by localized surface plasmon resonance changes depending on the position, and therefore, the degree of enhancement of fluorescence emitted by the fluorescent material 107 differs depending on the position at which the complex is formed and the position of the fluorescent material 107 in a free state.

For example, the fluorescent material 107 in a complex located in the gap between the metal micro protrusions 201 in the bottom right of FIG. 2 radiates fluorescence 110a enhanced by the locally enhanced electric field. The fluorescent material 107 in a complex in the vicinity of the gap around the center of FIG. 2 radiates fluorescence 110b also enhanced by the locally enhanced electric field. The fluorescent material 107 in a complex located at the top of the metal micro protrusion 201 radiates fluorescence 110c also enhanced by the locally enhanced electric field. The electric field intensity in the gap is extremely larger than the electric field intensity in the opening between the metal micro protrusions 201 and that at the top of the metal micro protrusion 201, and therefore, the fluorescence 110a has higher luminance. Accordingly, depending on the position of binding to the metal micro protrusion 201, the degree of enhancement of fluorescence emitted by the fluorescent material 107 differs.

The fluorescent material 107 that does not bind to the metal micro protrusion 201 and is in a free state may be affected by localized plasmon resonance depending on the position and the distance from the metal micro protrusion 201. For example, the fluorescent material 107 in a free state on the left of FIG. 2 is located in the opening of the gap between the metal micro protrusions 201 adjacent to each other, and therefore, radiates fluorescence 110e enhanced by the locally enhanced electric field. The fluorescence 110e may also be detected as surface enhanced fluorescence.

However, when the fluorescent material 107 in a free state exists at a position at which the fluorescent material 107 is not affected by localized surface plasmon resonance, fluorescence, such as fluorescence 112a, emitted by the fluorescent material 107 is original fluorescence of the fluorescent material 107.

Even when there is no effect of localized surface plasmon resonance, the fluorescence intensity increases due to, for example, aggregation of particles of the fluorescent material 107, and erroneous detection as surface enhanced fluorescence may occur. For example, an aggregate of particles of the fluorescent material 107 in the top left of FIG. 2 has a particle size larger than a single particle of the fluorescent material 107, and therefore, radiates fluorescence 112b having a higher fluorescence intensity.

When the fluorescent material 107 binds to the metal micro protrusion 201 by nonspecific adsorption without the first substance 105 therebetween, fluorescence of the fluorescent material 107, such as fluorescence 110d or fluorescence 113, may be enhanced.

As described above, with the existing fluorescence method, fluorescence (surface enhanced fluorescence) of the fluorescent material 107 in a complex is detected on the basis of the fluorescence intensity, and therefore, fluorescence of the fluorescent material 107 that does not form a complex may be erroneously detected as surface enhanced fluorescence. Therefore, in the existing fluorescence method, a process for removing the fluorescent material 107 in a free state and a process for suppressing nonspecific adsorption to the metal micro protrusion 201 need to be performed. However, even when these processes are performed, it is difficult to prevent erroneous detection of surface enhanced fluorescence. Therefore, with the existing detection method based on the fluorescence intensity, it is difficult to detect the detection target substance 103 with high accuracy.

In view of the above issues, the present inventor has made a close study and consequently found that fluorescence emitted by a fluorescent material in a complex can be detected on the basis of a fluorescence lifetime specific to the fluorescent material (hereinafter referred to as the attenuation characteristic of fluorescence). The fluorescence lifetime of a fluorescent material is specific to the fluorescent material and is not affected by variation in the particle size of the fluorescent material, aggregation, and the detection position. The fluorescence lifetime of a fluorescent material depends on the environment around the fluorescent material. For example, in a case where a substance (in the above example, the second substance 109) labeled with a fluorescent material changes or in a case where a substance labelled with a fluorescent material binds to another substance (in the above example, the detection target substance 103 or the metal micro protrusion 201), the radiative transition ratio or the non-radiative transition ratio increases, and therefore, the fluorescence lifetime decreases.

Overview of the Present Disclosure

A detection device according to an aspect of the present disclosure is a detection device for detecting a detection target substance by using a metal material modified with a first substance having a property of specifically binding to the detection target substance and a fluorescent material modified with a second substance having a property of specifically binding to the detection target substance, the detection device including: a light source that emits light for exciting the fluorescent material; a photodetector that detects fluorescence emitted by the fluorescent material over time for a specific period from when emission of the light by the light source is stopped; and a processor that detects the detection target substance in a complex formed of the metal material, the detection target substance, and the fluorescent material binding to each other, on the basis of an attenuation characteristic of the fluorescence during the specific period.

Fluorescent materials each have a fluorescence lifetime specific thereto, and therefore, the attenuation characteristic of fluorescence can be derived in accordance with the fluorescent material in use. The fluorescence lifetime (the attenuation characteristic of fluorescence) changes in accordance with the binding state of the fluorescent material, and therefore, the fluorescence lifetime of the fluorescent material in the complex and the fluorescence lifetime of the fluorescent material in a free state can be distinguished from each other. Therefore, with the above-described configuration, the fluorescence of the fluorescent material in the complex can be detected on the basis of the derived attenuation characteristic of the fluorescence, and detection accuracy for the detection target substance is increased.

For example, in the detection device according to the aspect of the present disclosure, the attenuation characteristic of the fluorescence may be expressed by a time from when the light source stops emitting the light to when an intensity of the fluorescence emitted by the fluorescent material is attenuated to a specific intensity, and the processor may detect the detection target substance in the complex in a case where the time is less than or equal to a threshold time.

As described above, the fluorescence lifetime specific to the fluorescent material in use can be derived as the time (hereinafter also referred to as an attenuation time) until the fluorescence of the fluorescent material is attenuated to the specific intensity. For fluorescence enhanced by localized surface plasmon resonance, the time until the fluorescence is attenuated to the specific intensity is shorter than the attenuation time specific to the fluorescent material. Therefore, when a time shorter than the attenuation time specific to the fluorescent material is used as the threshold time and fluorescence that is attenuated in a time less than or equal to the threshold time is detected, fluorescence of the fluorescent material in the complex can be detected. Therefore, according to the aspect of the present disclosure, detection accuracy for the detection target substance is increased.

For example, in the detection device according to the aspect of the present disclosure, the attenuation characteristic of the fluorescence may be expressed by an attenuation ratio that is a ratio of an amount of attenuation of an intensity of the fluorescence to a maximum intensity of the fluorescence during a period from when the light source stops emitting the light to when a specific time elapses, and the processor may detect the detection target substance in the complex in a case where a value of the attenuation ratio is greater than or equal to a threshold.

As described above, the fluorescence lifetime specific to the fluorescent material in use can be derived as the attenuation ratio of the fluorescence of the fluorescent material. The attenuation ratio of fluorescence enhanced by localized surface plasmon resonance is larger than the attenuation ratio of fluorescence specific to the fluorescent material. Therefore, when an attenuation ratio larger than the attenuation ratio of fluorescence specific to the fluorescent material is used as the threshold and fluorescence that is attenuated at an attenuation ratio greater than or equal to the threshold is detected, the fluorescence of the fluorescent material in the complex can be detected. Therefore, according to the aspect of the present disclosure, detection accuracy for the detection target substance is increased.

For example, in the detection device according to the aspect of the present disclosure, the processor may determine whether an intensity of the fluorescence detected by the photodetector is greater than or equal to a threshold intensity, and in a case where the intensity of the fluorescence is greater than or equal to the threshold intensity, detect the detection target substance in the complex on the basis of the attenuation characteristic of the fluorescence.

As described above, when it is determined whether the intensity of the fluorescence is greater than or equal to the threshold, the effect of fluorescence caused by nonspecific adsorption of the fluorescent material can be reduced. Accordingly, detection accuracy for the detection target substance is increased.

For example, in the detection device according to the aspect of the present disclosure, the metal material may be in a form of particles.

Accordingly, a solution that contains complexes is subjected to, for example, flow cytometry or an External Force-Assisted Near-field Illumination (EFA-NI) biosensor, and fluorescence of the fluorescent material in each complex can be detected individually.

For example, in the detection device according to the aspect of the present disclosure, the metal material may be a metal microstructure provided on a substrate.

Accordingly, the surface area of the metal material increases, and therefore, the metal material and the detection target substance are more likely to bind to each other. Accordingly, the complex is more likely to be formed, and detection accuracy is increased.

For example, in the detection device according to the aspect of the present disclosure, the metal material may contain, as a main component, metal on which localized surface plasmon resonance corresponding to a frequency of the light emitted by the light source or a fluorescence frequency of the fluorescent material occurs.

Accordingly, fluorescence emitted by the fluorescent material in the complex is enhanced by localized surface plasmon resonance that occurs on the metal material in the complex and is detected as fluorescence having a high fluorescence intensity (that is, surface enhanced fluorescence). In contrast, the fluorescent material that does not form the complex is not in the vicinity of the metal material spatially, and therefore, fluorescence emitted by the fluorescent material is not enhanced by localized surface plasmon resonance occurring on the metal material and has a fluorescence intensity much lower than that of fluorescence emitted by the fluorescent material in the complex. Therefore, with the above-described configuration, detection sensitivity for the detection target substance can be increased.

A detection method according to an aspect of the present disclosure is a detection method for detecting a detection target substance by using a metal material modified with a first substance having a property of specifically binding to the detection target substance and a fluorescent material modified with a second substance having a property of specifically binding to the detection target substance, the detection device method including: emitting light for exciting the fluorescent material; detecting fluorescence emitted by the fluorescent material over time for a specific period from when emission of the light is stopped; and detecting the detection target substance in a complex formed of the metal material, the detection target substance, and the fluorescent material binding to each other, on the basis of an attenuation characteristic of the fluorescence during the specific period.

Fluorescent materials each have a fluorescence lifetime specific thereto, and therefore, the attenuation characteristic of fluorescence can be derived in accordance with the fluorescent material in use. The fluorescence lifetime (the attenuation characteristic of fluorescence) changes in accordance with the binding state of the fluorescent material, and therefore, the fluorescence lifetime of the fluorescent material in the complex and the fluorescence lifetime of the fluorescent material in a free state can be distinguished from each other. Therefore, with the above-described configuration, the fluorescence of the fluorescent material in the complex can be detected on the basis of the derived attenuation characteristic of the fluorescence, and detection accuracy for the detection target substance is increased.

It should be noted that these general or specific aspects may be implemented as a system, a method, an integrated circuit, a computer program, or a computer-readable recording medium such as a CD-ROM or may be implemented as a combination of any of a system, a method, an integrated circuit, a computer program, and a recording medium.

Hereinafter, embodiments will be specifically described with reference to the drawings.

Note that any of the embodiments described below is a general or specific example. Numerical values, forms, materials, constituent elements, the arrangements and connections of constituent elements, steps, the order of steps, and so on described in the following embodiments are illustrative and are not intended to limit the scope of the claims. Among the constituent elements described in the following embodiments, a constituent element not described in an independent claim stating the most generic concept will be described as an optional constituent element. Furthermore, each diagram is not necessarily a precise diagram. In the diagrams, configurations that are substantially the same are assigned the same reference numerals, and a duplicated description thereof may be omitted or briefly given.

Further, in the following description, terms, such as parallel and vertical, denoting relationships between elements, terms, such as a cylindrical form and so on, denoting the forms of elements, and numerical ranges not only have their precise meanings but also have meanings that include substantially the same range, such as an error of about several percent.

Further, in the following description, detecting a detection target substance includes, in addition to detecting a detection target substance and confirming the presence of the detection target substance, measuring the amount of the detection target substance (for example, the number or concentration) or the range of the amount.

First Embodiment

Overview of Detection Device

Figure 3:
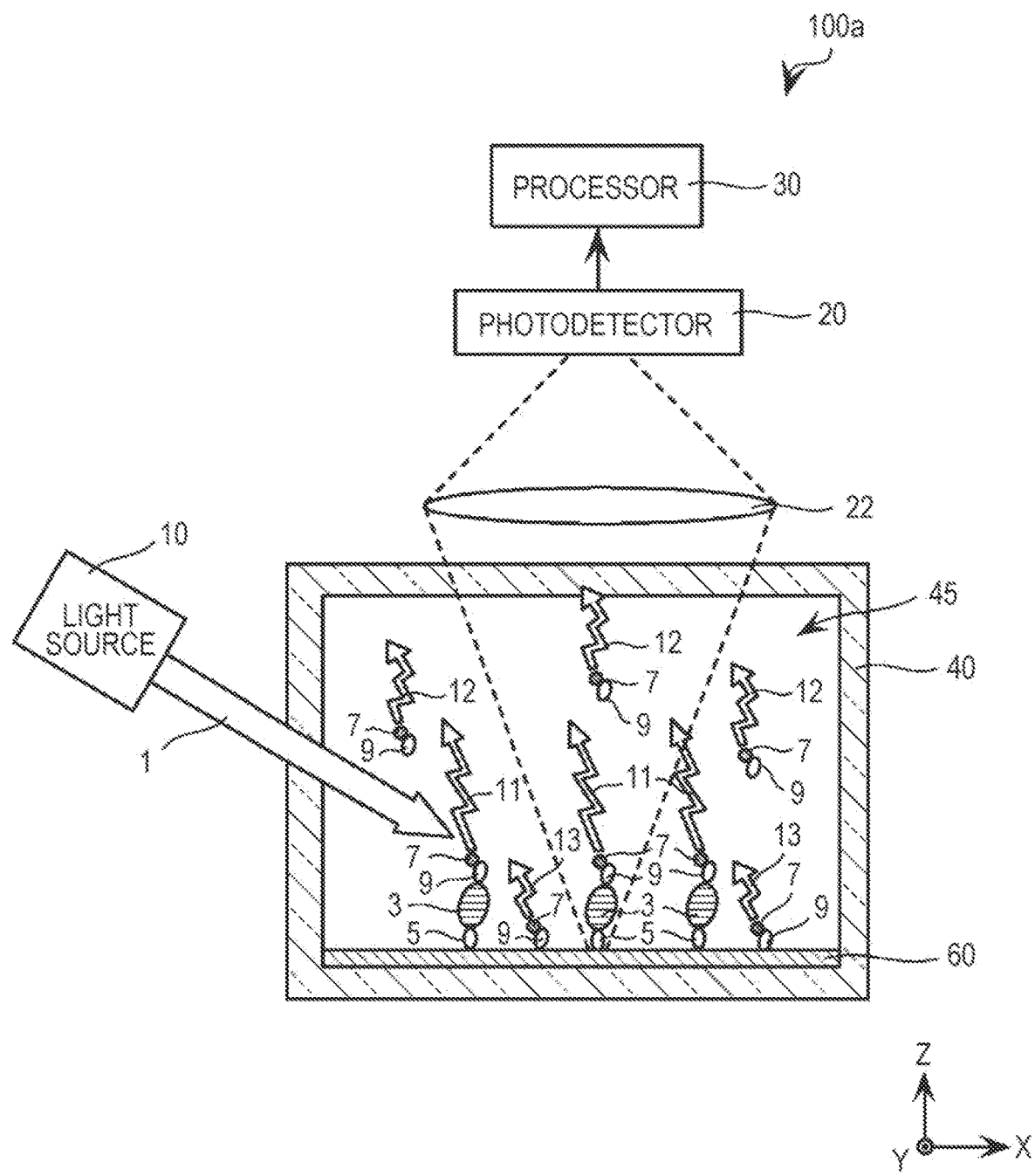
FIG. 3 is a schematic configuration diagram illustrating an example of a detection device according to a first embodiment.

First, the overview of a detection device according to a first embodiment will be described. FIG. 3 is a schematic configuration diagram illustrating an example of a detection device 100a according to the first embodiment, Note that FIG. 3 also illustrates a configuration for specifically explaining an example of a fluorescence method to be used in the detection device 100a.

The detection device 100a detects a detection target substance 3 by using a metal material 50a (see FIG. 4) modified with a first substance 5 having the property of specifically binding to the detection target substance 3 and a fluorescent material 7 modified with a second substance 9 having the property of specifically binding to the detection target substance 3. More specifically, the detection device 100a excites the fluorescent material 7 with light 1 emitted from a light source 10, detects fluorescence 11, fluorescence 12, and fluorescence 13 of the fluorescent material 7 over time for a specific period from when emission of the light 1 from the light source 10 is stopped, and uses the results of detection to detect a complex formed of the metal material 50a, the detection target substance 3, and the fluorescent material 7 binding to each other, on the basis of the attenuation characteristics of the fluorescence 11 to the fluorescence 13 during the specific period. Accordingly, the detection device 100a detects the detection target substance 3. That is, when the detection device 100a detects a complex, the detection device 100a determines that the detection target substance 3 is detected.

The detection target substance 3 is, for example, protein, lipid, sugar, or a nucleic acid. For example, the detection target substance 3 may be protein or a nucleic acid that forms a virus or may be a phospholipid or a sugar chain that is a component of the cell membrane of a virus. These substances are not limited to substances derived from viruses and may be substances derived from, for example, bacteria, mold, animals, plants, or insects. The substances may include, for example, an allergen, such as pollen.

The first substance 5 has the property of specifically binding to the detection target substance 3. The first substance 5 is immobilized on the metal material 50a. For example, in a case where the detection target substance 3 is protein that forms a virus, the first substance 5 is an antibody for the protein that is an antigen.

The metal material 50a (see FIG. 4) traps the detection target substance 3 with the first substance 5 therebetween. The metal material 50a may be disposed throughout the main surface of a sensor substrate 60 or may be disposed in a part of the main surface. The metal material 50a needs to be capable of specifically binding to the detection target substance 3 to trap the detection target substance 3. The metal material 50a may be in the form of particles or may be a metal microstructure provided on the substrate. In this embodiment, the metal material 50a is a metal microstructure provided on the substrate. The specific structure of the metal material 50a will be described below with reference to FIG. 4 and FIG. 5.

The metal material 50a may contain, as a main component, metal on which localized surface plasmon resonance occurs when excited by light emitted from the light source 10. The metal is, for example, gold, silver, aluminum, or an alloy that contains any metal among gold, silver, and aluminum as a main component. Accordingly, with light emitted from the light source 10, surface plasmons are excited in metal particles that form the metal material 50a, and this can cause localized surface plasmon resonance on the metal material 50a. At this time, a wavelength range in which the localized surface plasmon resonance occurs and the wavelength range of the light for exciting the fluorescent material 7 overlap, and therefore, fluorescence emitted by the fluorescent material 7 that is in the vicinity of the metal material 50a is enhanced by the effect of the localized surface plasmon resonance. The fluorescence is also enhanced in a phenomenon where the excitation energy of the fluorescent material 7 excites surface plasmons corresponding to the fluorescence frequency of the fluorescent material 7 due to energy transfer to the metal material 50a and where the excited surface plasmons are converted to light due to, for example, Bragg scattering. The fluorescence enhanced by these effects is called surface enhanced fluorescence. As described above, fluorescence of the fluorescent material 7 is enhanced by localized surface plasmon resonance, and therefore, the detection sensitivity for the detection target substance 3 is increased.

The second substance 9 has the property of specifically binding to the detection target substance 3. The second substance 9 is labelled with the fluorescent material 7. For example, in a case where the detection target substance 3 is protein that forms a virus, the second substance 9 is an antibody for the protein that is an antigen.

As illustrated in FIG. 3, the first substance 5 and the second substance 9 bind to the detection target substance 3 in different portions respectively. More specifically, the first substance 5 and the second substance 9 bind to the detection target substance 3 such that the detection target substance 3 is sandwiched between the first substance 5 and the second substance 9 (sandwich binding).

The first substance 5 and the second substance 9 may be any substances as long as the substances have the property of specifically binding to the detection target substance 3 and may have any molecular structure. The first substance 5 and the second substance 9 may be molecules of the same type or molecules of different types. The first substance 5 and the second substance 9 do not bind to each other and exist as separate substances.

The fluorescent material 7 emits fluorescence when excitation light having a specific wavelength is applied thereto. The fluorescent material 7 contains, for example, inorganic ceramic containing, for example, a rare-earth element or a transition metal element as an activator, organic fluorescent molecules, or semiconductor quantum dots. The fluorescent material 7 may be, for example, surface-modified with a hydrophilic group to make the fluorescent material 7 more dispersive in water, or the surface thereof may be coated with, for example, a resin that contains an anti-deactivation agent for fluorescence to suppress light fading of fluorescence.

Configuration of Detection Device

Figure 4:
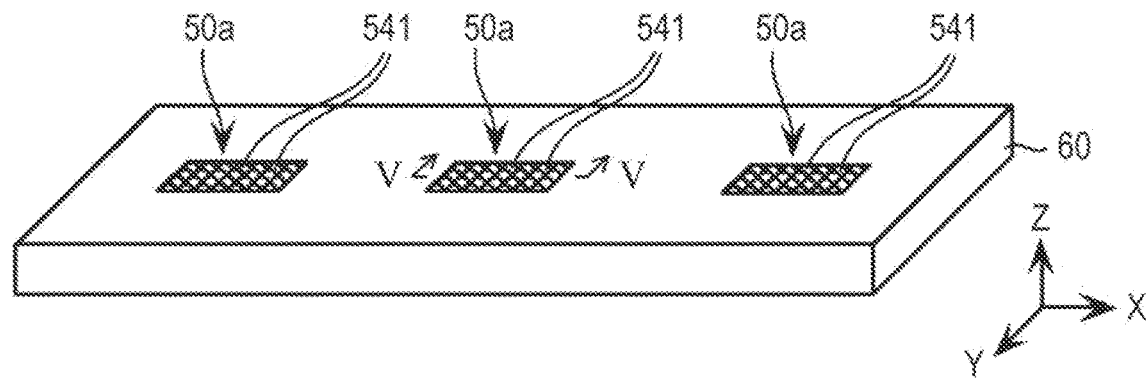
FIG. 4 is a perspective view of an example of a sensor substrate in the first embodiment.
Figure 5:
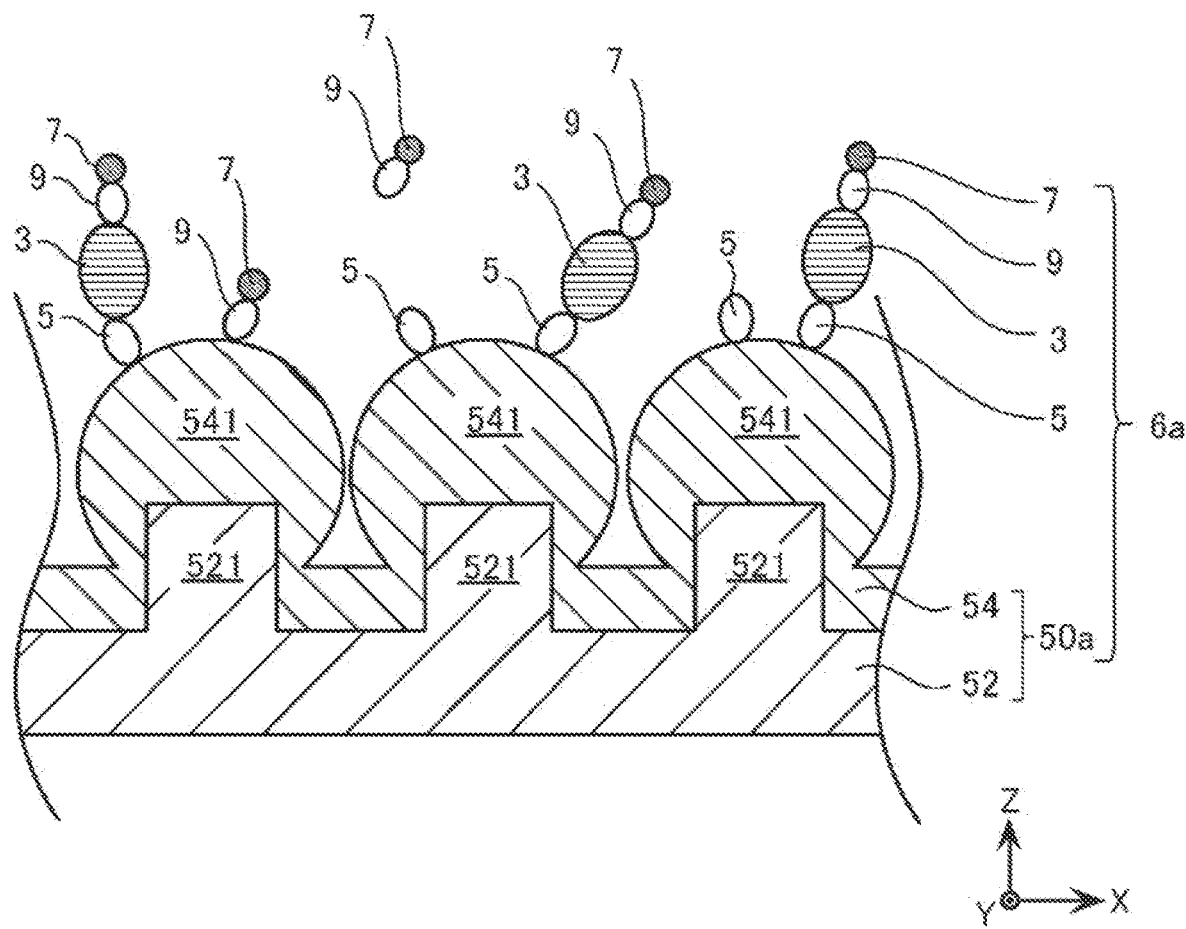
FIG. 5 is a schematic cross-sectional view cut along line V-V in FIG. 4.

Next, the configuration of the detection device 100a will be described with reference to FIG. 3 to FIG. 5. FIG. 4 is a perspective view of an example of the sensor substrate 60. FIG. 5 is a schematic cross-sectional view cut along line V-V in FIG. 4.

As illustrated in FIG. 3, the detection device 100a includes the light source 10, a photodetector 20, a processor 30, and a sensor cell 40.

The light source 10 emits the light 1 for exciting the fluorescent material 7. The light source 10 emits, for example, the light 1 having a specific wavelength to an irradiation region. The irradiation region is an example of a specific region and is a part of a region in the sensor cell 40. That is, the light source 10 emits the light 1 for exciting the fluorescent material 7 to a part of a mixed solution 45 in the sensor cell 40. As the specific wavelength, a wavelength with which the fluorescent material 7 can be excited and that can induce surface plasmon resonance on the metal material 50a disposed on the sensor substrate 60 is used. The mixed solution 45 is a solution that contains the detection target substance 3 and the fluorescent material 7 modified with the second substance 9.

The photodetector 20 detects fluorescence emitted by the fluorescent material 7 over time for a specific period from when emission of light by the light source 10 is stopped. The photodetector 20 receives fluorescence emitted from the fluorescent material 7 in the irradiation region of the light 1 for exciting the fluorescent material 7 and outputs an electric signal corresponding to the intensity of the fluorescence. The photodetector 20 receives the fluorescence via an optical system 22 formed of a primary optical lens, an optical filter, and a secondary optical lens.

The primary optical lens converts light from the irradiation region in the sensor cell 40 to substantially parallel light. Here, the light from the irradiation region includes scattered light in addition to the fluorescence 11 (surface enhanced fluorescence), the fluorescence 12, and the fluorescence 13. The optical filter blocks the light 1 for exciting the fluorescent material 7 and transmits wavelength components of the fluorescence 11, the fluorescence 12, and the fluorescence 13. The primary optical lens and the optical filter need not be configured as described above.

The processor 30 detects the detection target substance 3 in a complex 6*a* (see FIG. 5) formed of the metal material 50*a*, the detection target substance 3, and the fluorescent material 7 binding to each other, on the basis of the attenuation characteristic of fluorescence during the specific period. The attenuation characteristic of fluorescence is expressed by the time from when the light source 10 stops emitting the light 1 to when the intensity of fluorescence emitted by the fluorescent material 7 is attenuated to a specific intensity. The processor 30 derives the time until the intensity of fluorescence emitted by the fluorescent material 7 is attenuated to the specific intensity on the basis of the amount of change in an output signal of the photodetector 20 (that is, the amount of change in the intensity of fluorescence). In a case where the time is less than or equal to a threshold time, the processor 30 detects the detection target substance 3 in the complex 6*a*. The attenuation characteristic of fluorescence may be expressed by an attenuation ratio that is the ratio of the amount of attenuation of the intensity of fluorescence to the maximum intensity of the fluorescence during the period from when the light source 10 stops emitting the light 1 to when a specific time elapses. In this case, the processor 30 detects the detection target substance 3 in the complex 6*a* in a case where the value of the attenuation ratio is greater than or equal to a threshold.

Note that the processor 30 may determine whether the intensity of fluorescence detected by the photodetector 20 is greater than or equal to a threshold and in a case where the intensity of the fluorescence is greater than or equal to the threshold intensity, detect the detection target substance 3 in the complex 6*a* on the basis of the attenuation characteristic of the fluorescence.

The sensor cell 40 accommodates the mixed solution 45 that contains the detection target substance 3 and the fluorescent material 7 modified with the second substance 9. On the bottom of the sensor cell 40, the sensor substrate 60 is disposed. For example, the sensor cell 40 is a substantially cuboid container and has at least one transparent surface for transmitting excitation light and fluorescence. The sensor cell 40 illustrated in FIG. 3 is an optical cell, all surfaces of which are transparent. In FIG. 3, the light 1 for exciting the fluorescent material 7 enters the sensor cell 40 through the left-hand surface, and fluorescence exits the sensor cell 40 through the top surface.

The sensor substrate 60 is a substrate for trapping the detection target substance 3 on the surface and allowing the trapped detection target substance 3 to bind to the fluorescent material 7, thereby optically detecting the detection target substance 3. On the surface of the sensor substrate 60, particles of the first substance 5 are immobilized. As described above, the first substance 5 has the property of specifically binding to the detection target substance 3. Therefore, the sensor substrate 60 can trap the detection target substance 3 in the mixed solution 45 with the first substance 5 therebetween.

The sensor substrate 60 includes the metal material 50*a* modified with the first substance 5. For example, as illustrated in FIG. 4, the sensor substrate 60 includes at least one metal material 50*a* on the main surface on a side (the plus side of the Z axis) that is in contact with the mixed solution. Accordingly, the sensor substrate 60 traps the detection target substance 3 in the mixed solution 45 with the first substance 5 therebetween with which the metal material 50*a* is modified (in other words, the first substance 5 that binds to the metal material 50*a*).

As illustrated in FIG. 4 and FIG. 5, the metal material 50*a* is a metal microstructure formed of protruding microstructures 541. The metal material 50*a* includes a base material 52 that has protrusions 521 in at least a part of the main surface on one side, and a metal film 54 that covers the protrusions 521 on the base material 52. Accordingly, the protruding microstructures 541 that respectively correspond to the protrusions 521 are formed. The protruding microstructures 541 may be formed by forming a metal film on a base material having no protrusions 521 and directly micromachining the metal film. The protruding microstructures 541 thus formed are called a metal microstructure.

Operation of Detection Device

Figure 6:
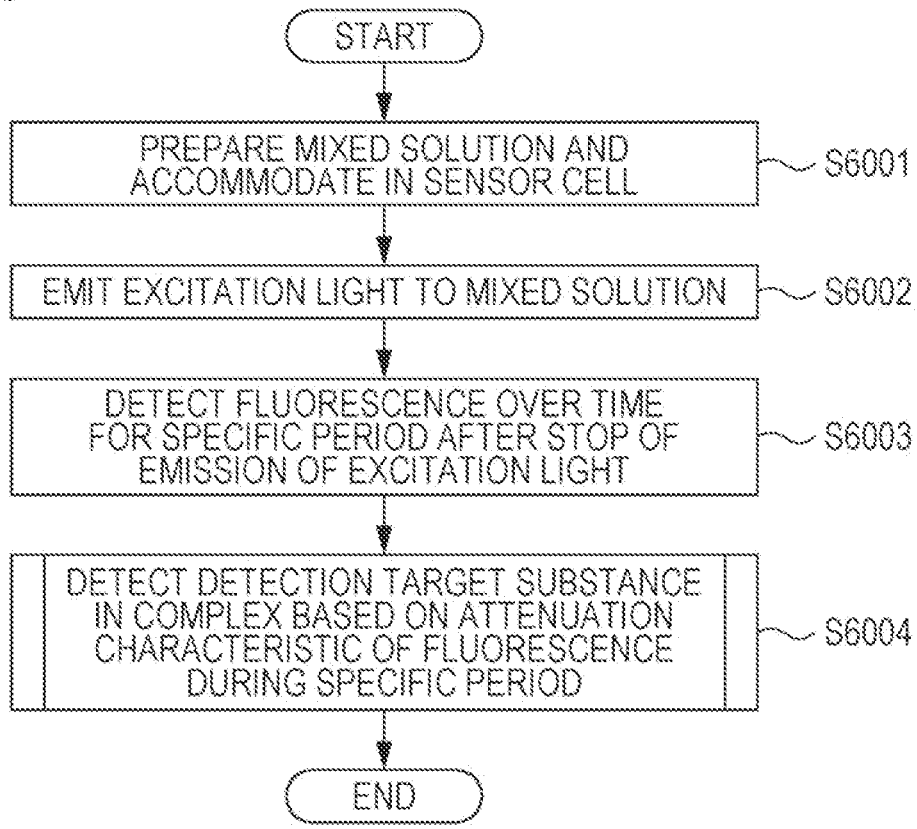
FIG. 6 is a flowchart illustrating an example operation of the detection device according to the first embodiment.
Figure 7:
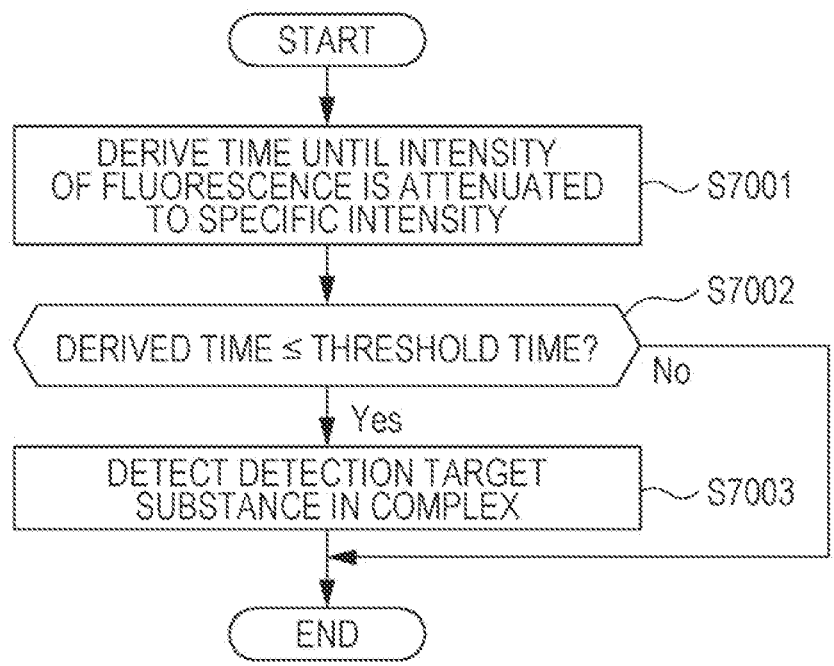
FIG. 7 is a flowchart illustrating an example detailed process flow in a step in FIG. 6.

Next, an operation of the detection device 100*a* will be described with reference to FIG. 6 to FIG. 8. FIG. 6 is a flowchart illustrating an example operation of the detection device 100*a* according to the first embodiment. FIG. 7 is a flowchart illustrating an example detailed process flow in step S6004 in FIG. 6. FIG. 8 is a flowchart illustrating another example detailed process flow in step S6004 in FIG. 6.

Before describing the flow in FIG. 6, immobilization of the first substance 5 on the sensor substrate 60 will be described first. The surface of the sensor substrate 60 on which the metal material 50*a* is disposed is brought into contact with a solution that contains the first substance 5 under a specific condition to immobilize the first substance 5 on the surface of the metal material 50*a*. Thereafter, an excess amount of the first substance 5 is washed away with a cleaning liquid to clean the metal material 50*a*.

Subsequently, the mixed solution 45 prepared in advance is accommodated in the sensor cell 40 (step S6001). The mixed solution 45 is prepared by, for example, mixing a sample solution that can contain the detection target substance 3 and a solution that contains the fluorescent material 7 modified with the second substance 9.

Next, the light source 10 emits the light 1 for exciting the fluorescent material 7 to a specific region in the sensor cell 40 (step S6002). The light source 10 may be a light source that is driven by a pulsed or rectangular voltage or current to emit light corresponding to the voltage or current.

Next, after the light source 10 stops emitting the light 1, the photodetector 20 detects fluorescence over time for a specific period (step S6003). The specific period may be the time until the fluorescence intensity of the fluorescent material 7 decreases to 1/e (e: the base of natural logarithm) of a peak value or may be the time until the fluorescence intensity decreases to one-half thereof.

Next, the processor 30 detects the detection target substance 3 in the complex 6*a* on the basis of the attenuation characteristic of the fluorescence during the specific period (step S6004). For example, the attenuation characteristic of the fluorescence may be expressed by the time from when the light source 10 stops emitting the light 1 to when the intensity of the fluorescence emitted by the fluorescent material 7 is attenuated to a specific intensity. The specific intensity may be an intensity lie of a peak value or may be an intensity one-half thereof. In this case, the processor 30 derives the time until the intensity of the fluorescence is attenuated to the specific intensity as illustrated in FIG. 7 (step S7001). Next, the processor 30 determines whether the derived time is less than or equal to a threshold time (step S7002). If the derived time is less than or equal to the threshold time (Yes in step S7002), the processor 30 detects the detection target substance 3 in the complex 6a (step S7003). On the other hand, if the derived time is longer than the threshold time (No in step S7002), the processor 30 terminates the process.

The attenuation characteristic of the fluorescence may be expressed by an attenuation ratio that is the ratio of the amount of attenuation of the intensity of the fluorescence to the maximum intensity of the fluorescence during the period from when the light source 10 stops emitting the light 1 to when a specific time elapses. In this case, as illustrated in FIG. 8, the processor 30 derives the ratio (attenuation ratio) of the amount of attenuation of the intensity of the fluorescence to the maximum intensity of the fluorescence during the period from when emission of excitation light is stopped to when a specific time elapses (step S8001). Next, the processor 30 determines whether the derived value of the attenuation ratio of the intensity of the fluorescence is greater than or equal to a threshold (step S8002). If the derived value of the attenuation ratio of the intensity of the fluorescence is greater than or equal to the threshold (Yes in step S6002), the processor 30 detects the detection target substance 3 in the complex 6a (step S8003). On the other hand, if the derived value of the attenuation ratio of the intensity of the fluorescence is less than the threshold (No in step S8002), the processor 30 terminates the process.

With the method described above, the attenuation characteristic of the fluorescence can be derived on the basis of the fluorescence lifetime specific to the fluorescent material, and therefore, the thresholds can be set in accordance with the fluorescent material in use. The fluorescence lifetime (the attenuation characteristic of the fluorescence) changes depending on the binding state of the fluorescent material 7, and therefore, the fluorescence lifetime of the fluorescent material 7 in the complex 6a and the fluorescence lifetime of the fluorescent material 7 in a free state can be distinguishably detected. Therefore, with the method described above, fluorescence of the fluorescent material 7 in the complex 6a can be detected on the basis of the attenuation characteristic of the fluorescence, and the detection accuracy for the detection target substance 3 is increased.

The detection device 100a may perform the following process flow. FIG. 9 is a flowchart illustrating another example operation of the detection device 100a according to the first embodiment. The process flow from step S9001 to step S9003 in FIG. 9 is the same as that from step S6001 to step S6003 in FIG. 6, and therefore, a description thereof will be omitted here.

The processor 30 determines whether the intensity of the fluorescence detected by the photodetector 20 is greater than or equal to a threshold (step S9004). If the intensity of the fluorescence detected by the photodetector 20 is greater than or equal to the threshold (Yes in step S9004), the processor 30 detects the detection target substance 3 in the complex 6a on the basis of the attenuation characteristic of the fluorescence during the specific period (step S9005). On the other hand, if the intensity of the fluorescence detected by the photodetector 20 is less than the threshold (No in step S9004), the processor 30 terminates the process. Note that the detailed flow in step S9005 is the same as that described with reference to FIG. 7 and FIG. 8, and therefore, a description thereof will be omitted here.

As described above, when it is determined whether the intensity of the fluorescence is greater than or equal to the threshold, the effect of fluorescence caused by nonspecific adsorption of the fluorescent material 7 can be reduced. Accordingly, the detection accuracy for the detection target substance 3 is increased.

Advantages and so on

The detection device 100a according to the first embodiment is a detection device for detecting the detection target substance 3 by using the metal material 50a modified with the first substance 5 having the property of specifically binding to the detection target substance 3 and the fluorescent material 7 modified with the second substance 9 having the property of specifically binding to the detection target substance 3, the detection device 100a including: the light source 10 that emits the light 1 for exciting the fluorescent material 7; the photodetector 20 that detects fluorescence emitted by the fluorescent material 7 over time for a specific period from when emission of the light 1 by the light source 10 is stopped; and the processor 30 that detects the detection target substance 3 in the complex 6a formed of the metal material 50a, the detection target substance 3, and the fluorescent material 7 binding to each other, on the basis of the attenuation characteristic of the fluorescence during the specific period.

Fluorescent materials each have a fluorescence lifetime specific thereto, and therefore, the attenuation characteristic of fluorescence can be derived in accordance with the fluorescent material in use. The fluorescence lifetime (the attenuation characteristic of fluorescence) changes in accordance with the binding state of the fluorescent material 7, and therefore, the fluorescence lifetime of the fluorescent material 7 in the complex 6a and the fluorescence lifetime of the fluorescent material 7 in a free state can be distinguished from each other. Therefore, with the above-described configuration, the fluorescence of the fluorescent material 7 in the complex 6a can be detected on the basis of the derived attenuation characteristic of the fluorescence, and detection accuracy for the detection target substance 3 is increased.

For example, in the detection device 100a, the attenuation characteristic of the fluorescence may be expressed by the time from when the light source 10 stops emitting the light 1 to when the intensity of the fluorescence emitted by the fluorescent material 7 is attenuated to a specific intensity, and the processor 30 may detect the detection target substance 3 in the complex 6a in a case where the time is less than or equal to a threshold time.

As described above, the fluorescence lifetime specific to the fluorescent material in use can be derived as the time (hereinafter also referred to as an attenuation time until the fluorescence of the fluorescent material is attenuated to the specific intensity. For fluorescence enhanced by localized surface plasmon resonance, the time until the fluorescence is attenuated to the specific intensity is shorter than the attenuation time of fluorescence specific to the fluorescent material. Therefore, when a time shorter than the attenuation time of fluorescence specific to the fluorescent material is used as the threshold time and fluorescence that is attenuated in a time less than or equal to the threshold time is detected, fluorescence of the fluorescent material 7 in the complex 6a can be detected. Therefore, detection accuracy for the detection target substance is increased.

For example, in the detection device 100a, the attenuation characteristic of the fluorescence may be expressed by an attenuation ratio that is the ratio of the amount of attenuation of the intensity of the fluorescence to the maximum intensity of the fluorescence during a period from when the light source 10 stops emitting the light 1 to when a specific time elapses, and the processor 30 may detect the detection target substance 3 in the complex 6a in a case where the value of the attenuation ratio is greater than or equal to a threshold.

As described above, the fluorescence lifetime specific to the fluorescent material in use can be derived as the attenuation ratio of the fluorescence of the fluorescent material. The attenuation ratio of fluorescence enhanced by localized surface plasmon resonance is larger than the attenuation ratio of fluorescence specific to the fluorescent material. Therefore, when an attenuation ratio larger than the attenuation ratio of fluorescence specific to the fluorescent material is used as the threshold and fluorescence that is attenuated at an attenuation ratio greater than or equal to the threshold is detected, the fluorescence of the fluorescent material 7 in the complex 6a can be detected. Therefore, detection accuracy for the detection target substance 3 is increased.

For example, in the detection device 100a, the processor 30 may determine whether the intensity of the fluorescence detected by the photodetector 20 is greater than or equal to a threshold intensity, and in a case where the intensity of the fluorescence is greater than or equal to the threshold intensity, detect the detection target substance 3 in the complex 6a on the basis of the attenuation characteristic of the fluorescence.

As described above, when it is determined whether the intensity of the fluorescence is greater than or equal to the threshold, the effect of fluorescence caused by nonspecific adsorption can be reduced. Accordingly, detection accuracy for the detection target substance 3 is increased.

In the detection device 100a, the metal material 50a is a metal microstructure provided on the sensor substrate 60.

Accordingly, the surface area of the metal material 50a increases, and therefore, the metal material 50a and the detection target substance 3 are more likely to bind to each other. Accordingly, the complex 6a is more likely to be formed, and detection accuracy for the detection target substance 3 is increased.

For example, in the detection device 100a, the metal material 50a may contain, as a main component, metal on which localized surface plasmon resonance corresponding to the frequency of the light 1 emitted by the light source 10 or the fluorescence frequency of the fluorescent material 7 occurs.

Accordingly, fluorescence emitted by the fluorescent material 7 in the complex 6a is enhanced by localized surface plasmon resonance that occurs on the metal material 50a in the complex 6a and is detected as fluorescence having a high fluorescence intensity (that is, surface enhanced fluorescence). In contrast, the fluorescent material 7 that does not form the complex 6a is not in the vicinity of the metal material 50a spatially, and therefore, fluorescence emitted by the fluorescent material 7 is not enhanced by localized surface plasmon resonance occurring on the metal material 50a and has a fluorescence intensity much lower than that of fluorescence emitted by the fluorescent material 7 in the complex 6a. Therefore, with the above-described configuration, detection sensitivity for the detection target substance 3 can be increased.

Second Embodiment

Figure 10:
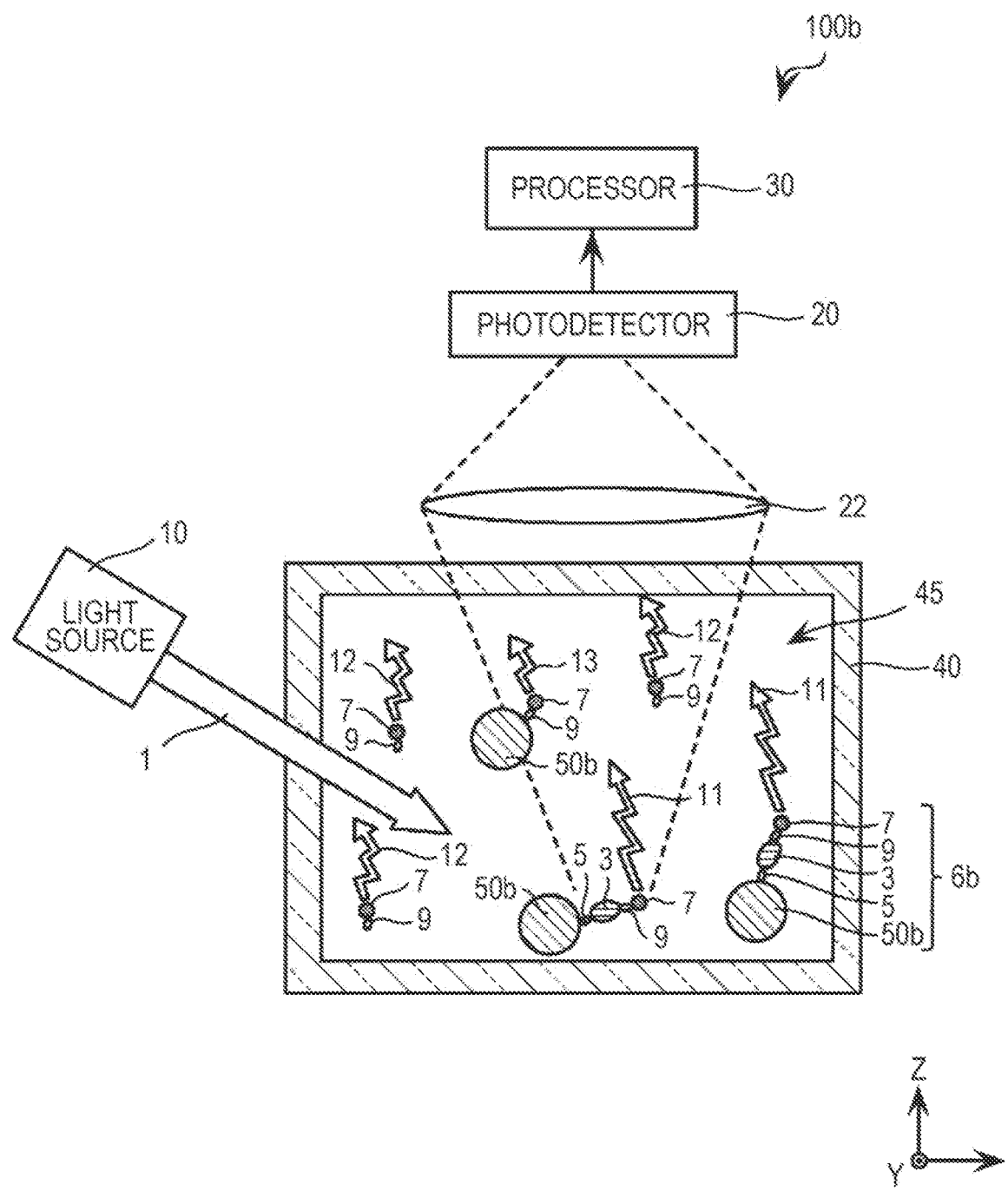
FIG. 10 is a schematic configuration diagram illustrating an example of a detection device according to a second embodiment.

Now, a detection device according to a second embodiment will be described with reference to FIG. 10. FIG. 10 is a schematic configuration diagram illustrating an example of a detection device 100b according to the second embodiment. Note that a configuration the same as that of the detection device 100a according to the first embodiment is assigned the same reference numeral, and a description thereof will be omitted. Differences from the first embodiment will be focused and described below.

Although the sensor cell 40 includes the sensor substrate 60 on the bottom in the detection device 100a according to the first embodiment, the detection device 100b according to the second embodiment does not include the sensor substrate 60. Although the sensor substrate 60 includes the metal material 50a that is a metal microstructure on the main surface on the side that is in contact with the mixed solution 45 containing the detection target substance 3 and the fluorescent material 7 in the first embodiment, the second embodiment uses a metal material 50b that is in the form of particles.

In the second embodiment, the metal material 50b is in the form of particles, and therefore, a complex 6b can be easily obtained by adding the metal material 50b to the mixed solution 45 and mixing the metal material 50b and the mixed solution 45. The metal material 50a disposed on the substrate needs to be cleaned in the process of forming the complex 6a. In a case where the metal material 50b is in the form of particles, the complex 6b can be easily formed because the cleaning process can be omitted. At this time, in the sensor cell 40, in addition to the complex 6b, the fluorescent material 7 that is in a free state and that does not form the complex 6b and the fluorescent material 7 that is nonspecifically adsorbed onto the metal material 50b are contained. The metal material 50b is in the form of particles, and therefore, these fluorescent materials in different binding forms can be detected as points of light.

The metal material 50b may contain, as a main component, metal on which localized surface plasmon resonance corresponding to the frequency of the light 1 emitted by the light source 10 or the fluorescence frequency of the fluorescent material 7 occurs. Accordingly, the metal material 50b can effectively cause localized surface plasmon resonance to occur.

For example, as illustrated in FIG. 10, when the light 1 for exciting the fluorescent material 7 is emitted from the light source 10, the fluorescence 11 emitted by the fluorescent material 7 in the complex 6b is enhanced by localized surface plasmon resonance (that is, surface enhanced fluorescence). The fluorescence 12 emitted by the fluorescent material 7 that is in a free state and that does not form the complex 6b is not affected by localized surface plasmon resonance. The fluorescence 13 emitted by the fluorescent material 7 that is nonspecifically adsorbed onto the metal material 50b has a low fluorescence intensity because the excitation energy of the fluorescent material 7 transfers to the metal material 50b, and therefore, the fluorescence lifetime is short.

Metal on which localized surface plasmon resonance occurs is, for example, gold, silver, aluminum, or an alloy that contains any metal among gold, silver, and aluminum as a main component. At this time, when the second substance 9 labeled with the fluorescent material 7 is nonspecifically adsorbed onto the surface of the metal material 50b, a quench phenomenon in which fluorescence from the fluorescent material 7 is not detected any more is likely to occur. The quench phenomenon is a fluorescence extinction phenomenon that is caused by energy directly transferring from the fluorescent material 7 to the metal material 50b and suffering thermal dissipation. In nonspecific adsorption, the distance between the fluorescent material 7 and the surface of the metal material 50b is short, and therefore, fluorescence extinction caused by the quench phenomenon is significant. In a case where the metal material 50*b* is made of gold, silver, aluminum, or an alloy that contains any metal among gold, silver, and aluminum as a main component, nonspecific adsorption can be suppressed, and therefore, the detection target substance can be detected with higher accuracy.

For example, in a case where the metal material 50*b* is made of gold, coating having various functions can be easily applied to the surface of the metal material 50*b*. For example, when anti-nonspecific-adsorption coating is applied to the surface of the metal material 50*b*, nonspecific adsorption in which the second substance 9 labeled with the fluorescent material 7 is adsorbed onto the surface of the metal material 50*b* can be suppressed. As a result, the possibility that a false positive detection result or a false negative detection result is obtained can be reduced.

Note that the sensor cell 40 may be a flow path through which a solution that can contain complexes can flow. In the second embodiment, the metal material 50*b* is in the form of particles, and therefore, when a solution that contains complexes is subjected to, for example, flow cytometry, fluorescence of the fluorescent material in each complex can be detected individually. Further, for a point of light having a luminance higher than a specific luminance, fluorescence emitted by the fluorescent material 7 in the complex 6*b* can be detected on the basis of the attenuation characteristic of the fluorescence of the fluorescent material 7, and therefore, the detection target substance 3 can be detected with higher accuracy.

Modification

Figure 11:
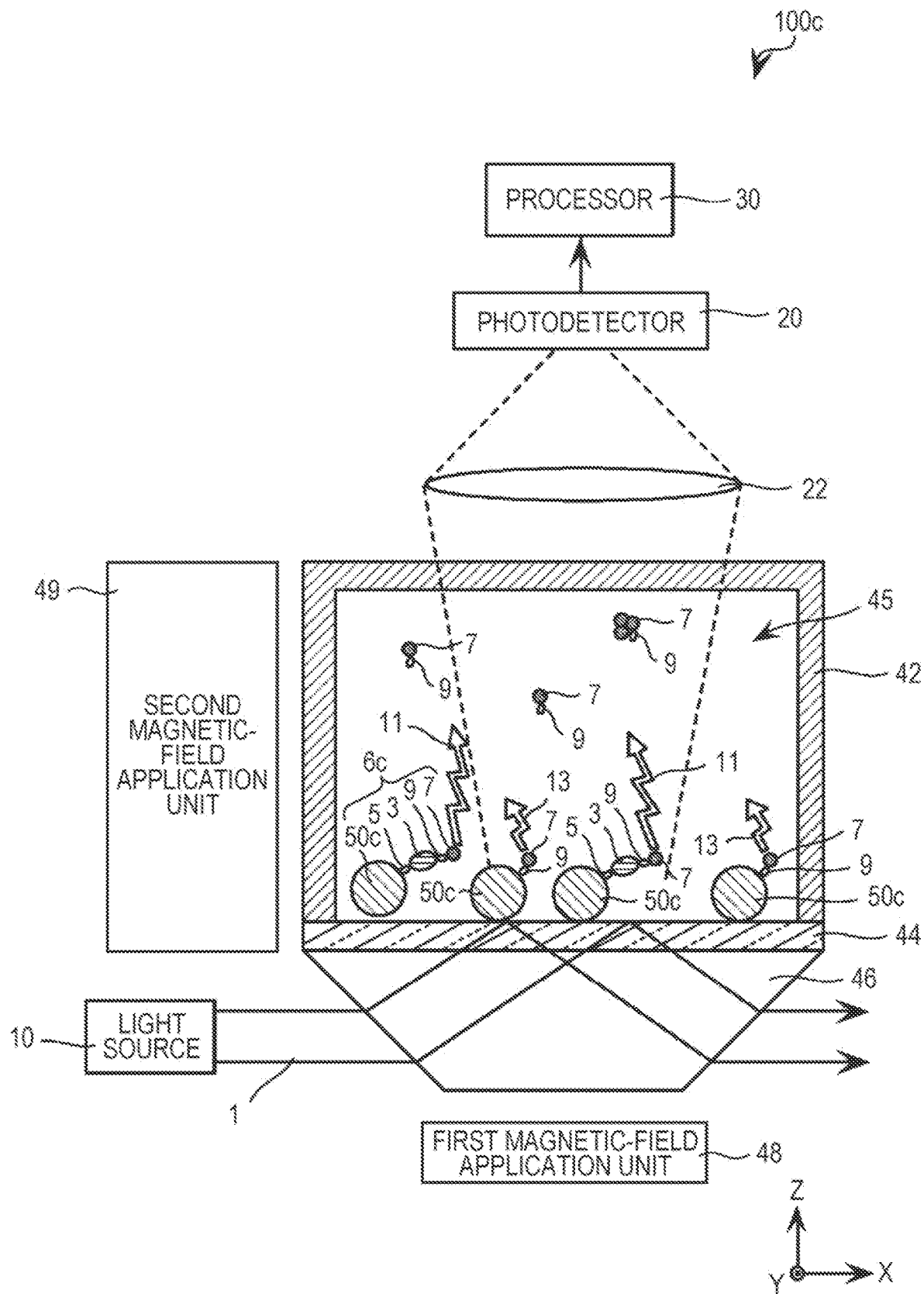
FIG. 11 is a schematic configuration diagram illustrating an example of a detection device according to a modification of the second embodiment.

Now, a detection device according to a modification of the second embodiment will be described with reference to FIG. 11. FIG. 11 is a schematic configuration diagram illustrating an example of a detection device 100*c* according to the modification of the second embodiment. Note that a configuration the same as that of the detection device 100*b* according to the second embodiment is assigned the same reference numeral, and a description thereof will be omitted. Differences from the second embodiment will be focused and described below.

A metal material 50*c* contains, for example, a magnetic material having paramagnetism. Paramagnetism is the property of not being magnetized when there is no external magnetic field but being weakly magnetized in response to application of a magnetic field, in the direction of application. The magnetic material having paramagnetism may be, for example, ferrite containing an iron oxide as a main component. Note that the magnetic material is not limited to ferrite and may be, for example, iron, sodium, aluminum, or platinum.

The metal material 50*c* may contain, as a main component, metal on which localized surface plasmon resonance corresponding to the frequency of the light 1 emitted by the light source 10 or the fluorescence frequency of the fluorescent material 7 occurs. In this case, the metal material 50*c* may have an inner core part (not illustrated) made of the above-described magnetic material and an outer shell part (not illustrated) covering the inner core part and made of a nonmagnetic metal material on which localized surface plasmon resonance occurs. Accordingly, when an external magnetic field is applied, the metal material 50*c* is magnetized in the direction of application and causes localized surface plasmon resonance to occur by the light 1 emitted from the light source 10.

Now, the configuration of the detection device 100*c* will be described. The detection device 100*c* is different from the detection device 100*b* according to the second embodiment in that the detection device 100*c* includes a light guiding unit 46, a sensor cell 42 including a detection panel 44, a first magnetic-field application unit 48, and a second magnetic-field application unit 49.

The sensor cell 42 includes the detection panel 44 on the bottom. The detection panel 44 is in contact with the light guiding unit 46 on a surface (back surface) opposite to the sensor cell 42. The back surface of the detection panel 44 and the light guiding unit 46 need to be in close contact with each other so as not to cause loss of the light 1 emitted from the light source 10 to the extent possible. For example, the detection panel 44 and the light guiding unit 46 are in contact with each other with refractive index matching oil therebetween. Note that the detection panel 44 and the light guiding unit 46 may be joined together by an adhesive layer. The detection panel 44 is a panel-like member having optical transparency. The detection panel 44 may be formed of a single layer or may be a layered structure formed of layers having different refractive indices.

The light guiding unit 46 guides the light 1 emitted from the light source 10 to the back surface of the detection panel 44, and the light 1 incident on the detection panel 44 from the back surface is totally reflected on the front surface of the detection panel 44. At this time, on a side opposite to the side on which the light 1 is reflected on the front surface of the detection panel 44, a nearfield, such as an evanescent field or an enhanced electric field, is formed. The nearfield is formed only in the vicinity of the front surface of the detection panel 44. The nearfield is an example of excitation light that exists in a limited region in the vicinity of the front surface of the detection panel 44. The light guiding unit 46 is implemented as, for example, a generally available prism.

The first magnetic-field application unit 48 generates a magnetic field gradient (hereinafter referred to as a first magnetic field gradient) in a first direction that extends toward the minus side in the Z-axis direction in FIG. 11 to attract the metal material 50*c* in the sensor cell 42. Accordingly, the metal material 50*c* in the sensor cell 42 moves to the front surface of the detection panel 44. The first magnetic-field application unit 48 may be made of a permanent magnet, such as a neodymium magnet, or may be made of, for example, a ferrite magnet containing an iron oxide and so on as main components or an alnico magnet containing aluminum, nickel, cobalt, and so on as main components.

The second magnetic-field application unit 49 generates a magnetic field gradient (hereinafter referred to as a second magnetic field gradient) in a second direction that extends toward the minus side in the X-axis direction in FIG. 11 to attract the metal material 50*c* that has moved to the front surface of the detection panel 44, in the second direction. Accordingly, the metal material 50*c* moves in the second direction along the front surface of the detection panel 44. Similar to the first magnetic-field application unit 48, the second magnetic-field application unit 49 may be made of a permanent magnet, such as a neodymium magnet, or may be made of, for example, a ferrite magnet or an alnico magnet.

Here, movement of the metal material 50*c* means that the position of the metal material 50*c* changes in the direction of the gradient of the applied magnetic field. Similarly, the position of a joined material that contains the metal material 50*c* also changes in the direction of the gradient of the applied magnetic field.

As described above, with the detection device 100*c* according to this modification, the metal material 50*c* is attracted to the front surface of the detection panel 44 on which a nearfield is generated, and the metal material 50*c* is further moved along the front surface of the detection panel 44. Accordingly, the photodetector 20 can detect the fluorescent material 7 in each complex 6c as a moving point of light individually. At this time, although the fluorescent material 7 nonspecifically adsorbed onto the metal material 50c is also detected as a moving point of light, the quench phenomenon is likely to occur as described above, and fluorescence extinction is significant accordingly. Therefore, the point of light has a luminance lower than the luminance of the fluorescent material 7 in the complex 6c such that no attention is required. Further, for a point of light having a luminance higher than a specific luminance, fluorescence emitted by the fluorescent material 7 in the complex 6c can be detected on the basis of the attenuation characteristic of the fluorescence of the fluorescent material 7, and therefore, the detection target substance 3 can be detected with higher accuracy.

EXAMPLES

The detection device of the present disclosure will be specifically described on the basis of examples. Note that the present disclosure is not limited to only the following examples.

In a first example and in first and second comparative examples, a sensor substrate, a fluorescent material, excitation light, and a photodetector described below were used.

Sensor Substrate

A metal microstructure (hereinafter referred to as a metal material 50d) formed of a two-dimensional grating having intervals of about 750 nm was used. The metal microstructure is made of gold as its metal material.

Fluorescent Material

As the fluorescent material, silicon quantum dots (hereinafter referred to as a fluorescent material 17) having a peak fluorescence wavelength around 850 nm were used.

Excitation Light

Oscillation light of 488 nm from an optical parametric oscillator using a third-order harmonic (355 nm) of an Nd:YAG laser as excitation light was used.

The pulse width of the Nd:YAG laser is 5 nanoseconds and the repetition cycle thereof is 20 Hz.

Photodetector

As the photodetector, an infrared photomultiplier tube containing InP/InGaAs on the photoelectric surface was used, and a fluorescence intensity at a wavelength of 850 nm and the response time were measured by using a spectroscope.

First Example

FIG. 12 includes diagrams schematically illustrating a positional relationship between the metal material 50d and the fluorescent material 17 in the first example, that in the first comparative example, and that in the second comparative example.

As illustrated in FIG. 12(a), in the first example, a transparent film (not illustrated) that functions as a spacer was disposed on the sensor substrate provided with the metal material 50d. On the transparent film, a specific amount of the fluorescent material 17 was disposed. The thickness of the transparent film that functions as a spacer was adjusted such that the distance D from the metal material 50d to the fluorescent material 17 is about 100 nm. This distance is substantially equivalent to the distance between the fluorescent material and the metal material in a complex formed by sandwich binding.

Figure 13:
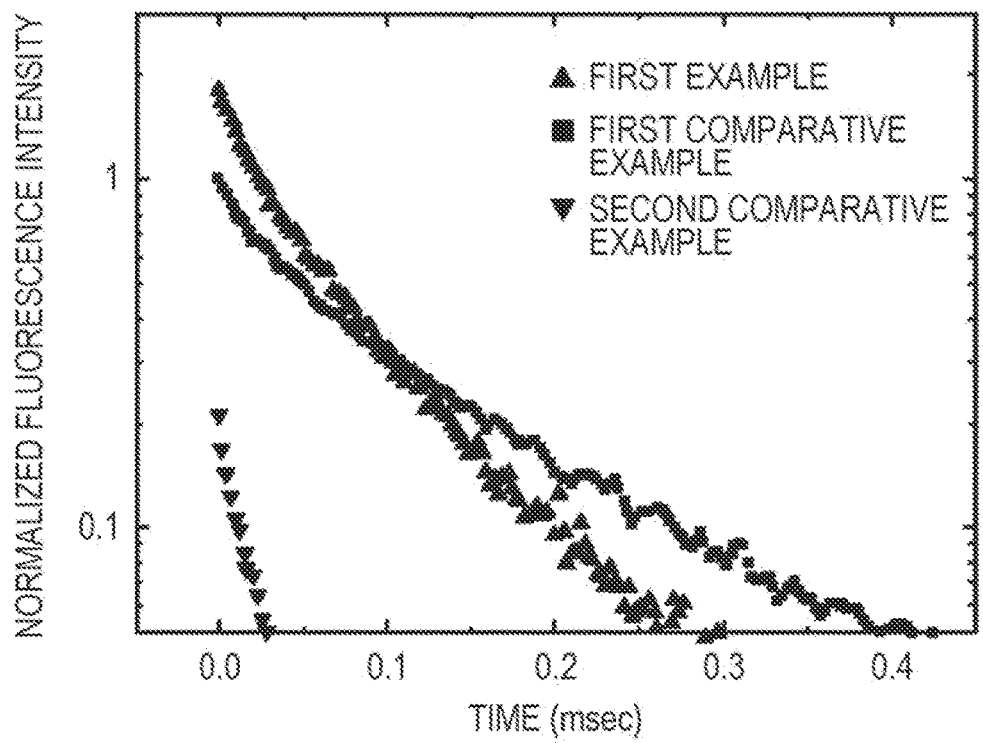
FIG. 13 is a diagram illustrating the attenuation characteristic of the fluorescence intensity of the fluorescent material in the first example, that in the first comparative example, and that in the second comparative example.
Figure 14:
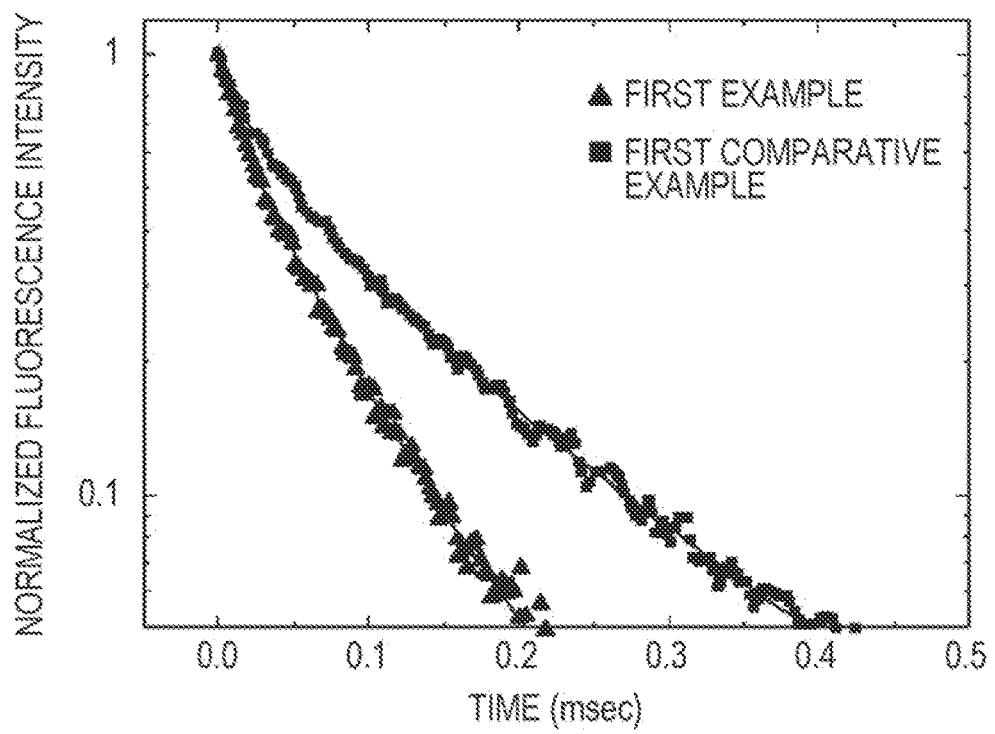
FIG. 14 is a diagram illustrating the attenuation characteristic of the fluorescence intensity of the fluorescent material in the first example and that in the first comparative example.

Emission of excitation light to the metal material 50d and to the fluorescent material 17 and conditions for detecting fluorescence emitted by the fluorescent material 17 are as described above. The results of detection of fluorescence emitted by the fluorescent material 17 are illustrated in FIG. 13 and FIG. 14. The results will be described below.

First Comparative Example

The first comparative example is the same as the first example except for the height of the spacer. As illustrated in FIG. 12(b), in the first comparative example, the height of the spacer was adjusted such that the distance D from the metal material 50d to the fluorescent material 17 is larger than 1 µm. This distance can be regarded as a sufficient distance with which almost no interaction in a nearfield occurs between the fluorescent material and the metal material.

The results of detection of fluorescence emitted by the fluorescent material 17 are illustrated in FIG. 13 and FIG. 14. The results will be described below.

Second Comparative Example

As illustrated in FIG. 12(c), a specific amount of the fluorescent material 17 was disposed directly on the sensor substrate provided with the metal material 50d. This represents a state where the fluorescent material is in contact with or in the close vicinity of the metal material due to, for example, nonspecific adsorption of the fluorescent material and the metal material.

The results of detection of fluorescence emitted by the fluorescent material 17 are illustrated in FIG. 13. The results will be described below.

Results

FIG. 13 is a diagram illustrating the attenuation characteristic of the fluorescence intensity of the fluorescent material in the first example, that in the first comparative example, and that in the second comparative example. Specifically, FIG. 13 is a graph that shows a relationship between the normalized fluorescence intensity of fluorescence of the fluorescent material and time. The normalized fluorescence intensity is a value obtained by normalization based on a fluorescence intensity when the time is 0 msec in the first comparative example. The time represents the elapsed time since the time when emission of excitation light is stopped, which is assumed to be 0 msec.

As indicated by small black triangles in FIG. 13, in the first example, the fluorescence intensity of the fluorescent material 17 when emission of excitation light was stopped was twice the fluorescence intensity in the first comparative example. However, the attenuation time of fluorescence was shorter than the attenuation time of fluorescence in the first comparative example.

From the results described above, it is found that in the first example, localized surface plasmon resonance occurred on the metal material 50d, and fluorescence of the fluorescent material 17 was enhanced accordingly. That is, the radiative transition ratio of the fluorescent material 17 increased due to interactions between the fluorescent material 17 and surface plasmons, and therefore, the fluorescence intensity of the fluorescent material 17 increased and the attenuation time of fluorescence became shorter.

As indicated by small black squares in FIG. 13, in the first comparative example, the fluorescent material 17 was sufficiently spaced apart from the metal material 50d, and the fluorescent material 17 was less likely to be affected by localized surface plasmon resonance, and therefore, the fluorescent material 17 exhibited a fluorescence lifetime (attenuation time of fluorescence) specific to the fluorescent material 17.

As indicated by small black inverted triangles in FIG. 13, in the second comparative example, the fluorescence intensity of the fluorescent material 17 when emission of excitation light was stopped was about one-tenth of the fluorescence intensity in the first example and about one-fifth of the fluorescence intensity in the first comparative example. In a case where the fluorescent material 17 and the metal material 50d are in contact with each other as in the second comparative example, a very large portion of excitation energy of the fluorescent material 17 is consumed as thermal dissipation in the metal. Therefore, the non-radiative transition ratio of the fluorescent material 17 increased, the fluorescence intensity of the fluorescent material 17 decreased, and the attenuation time of fluorescence became shorter.

In the second comparative example, although the fluorescent material 17 slightly emitted fluorescence, the fluorescent material 17 might not emit fluorescence at all depending on the degree of the quench phenomenon as described in the Underlying Knowledge Forming Basis of the Present Disclosure. Slight fluorescence as in the second comparative example is often excluded from a detection target.

Now, the attenuation characteristic (here, the attenuation time) of fluorescence in the first example and that in the first comparative example were compared with each other. FIG. 14 is a diagram illustrating the attenuation characteristic of fluorescence in the first example and that in the first comparative example. FIG. 14 illustrates a relationship between a normalized fluorescence intensity and time, the normalized fluorescence intensity being obtained by normalization while a fluorescence intensity at the time 0 msec in the first example and that in the first comparative example are assumed to be 1.

In addition to the plot of the normalized fluorescence intensity in the first example and that in the first comparative example, FIG. 14 also illustrates the results of fitting of the normalized fluorescence intensities with an exponential function as solid lines. Data obtained from the detector (hereinafter also referred to as detection data) includes noise, and therefore, when the obtained data is used as is to calculate the attenuation time of fluorescence, the result varies to a large degree. When the obtained data is subjected to fitting with, for example, an exponential function, the attenuation time of fluorescence can be calculated with high accuracy. FIG. 14 illustrates the results of fitting of detection data in the first example and that in the first comparative example with a stretched exponential function, as solid lines. Here, the attenuation time of fluorescence was calculated for the first example and the first comparative example from the detection data subjected to fitting. As the attenuation time of fluorescence, the time taken for the fluorescence intensity to be attenuated to 1/e of the maximum fluorescence intensity was calculated, where e denotes the base of natural logarithm.

As a result, the attenuation time of fluorescence in the first example was 47.7 μsec while that in the first comparative example was 82.4 μsec, and an obvious difference was observed.

Further, a threshold time was set on the basis of the original fluorescence lifetime of the fluorescent material (here, the first comparative example), and it was verified that in a case where the time taken for the fluorescence intensity of the fluorescent material to be attenuated to a specific intensity is less than or equal to the threshold time, a detection target substance in a complex could be detected.

From the above-described results, as in the first example and the first and second comparative examples, it was verified that fluorescence emitted by the fluorescent material was affected by, for example, localized surface plasmon resonance occurring on the metal material and by a thermal energy transition to the metal material in accordance with the distance to the metal material and that not only the fluorescence intensity changed but also the attenuation time of fluorescence changed. The fluorescence intensity of fluorescence emitted by the fluorescent material also changes in accordance with the particle size distribution of the fluorescent material, aggregation, and the detection position. However, in this case, the attenuation time (that is, the fluorescence lifetime) of fluorescence emitted by the fluorescent material is not affected by disturbance, such as local plasmon resonance, and therefore, does not change.

Therefore, thresholds were set for the fluorescence intensity and the attenuation time of fluorescence, fluorescence of the nonspecifically adsorbed fluorescent material (second comparative example) was first eliminated on the basis of the magnitude of the fluorescence intensity, and it was verified that fluorescence emitted by the fluorescent material in a complex and fluorescence emitted by the fluorescent material in a free state could be distinguishably detected on the basis of the attenuation time of fluorescence. As in the second comparative example, in a case of the fluorescent material nonspecifically adsorbed onto the metal material, the quench phenomenon occurs, and therefore, fluorescence of the fluorescent material can be detected so as to be distinguishable from surface enhanced fluorescence in actual detection. Therefore, it is considered that when only a threshold of the attenuation time of fluorescence is set, fluorescence of the fluorescent material in a complex can be detected so as to be distinguishable from fluorescence of the fluorescent material in a free state. Although verification was made on the basis of, for example, the attenuation time of fluorescence, a threshold may be set for the attenuation ratio of fluorescence.

Although a sensor substrate provided with a metal microstructure, which is the metal material 50d, was used in the first example and in the first and second comparative examples, the metal material may be metal microparticles. Also in a case of using surface plasmon resonance by metal microparticles, it is considered that results similar to those described above can be obtained.

Other Embodiments

Although the detection device and the detection method according to one or more aspects of the present disclosure have been described on the basis of the above-described embodiments, the present disclosure should not be limited to the embodiments. Any embodiment obtained by making various modifications conceived by a person skilled in the art to the embodiments and any embodiment obtained by combining constituent elements in different embodiments may be included in the scope of one or more aspects of the present disclosure without departing from spirit of the present disclosure.

Some or all of the constituent elements included in the detection device according to the above-described embodiments may be formed as one system LSI (Large Scale Integration) circuit. For example, the detection device may be formed as a system LSI circuit that includes the light source, the photodetector, and the processor. Note that the system LSI circuit need not include the light source.

The system LSI circuit is an ultra-multifunction LSI circuit that is manufactured by integrating constituent units on one chip, and specifically is a computer system that includes a microprocessor, a ROM (read-only memory), a RAM (random access memory), and so on. In the ROM, a computer program is stored. When the microprocessor operates in accordance with the computer program, the system LSI circuit implements its functions.

Although the system LSI circuit is mentioned here, the system LSI circuit may be called an IC, an LSI circuit, a super LSI circuit, or an ultra LSI circuit depending on the difference in the degree of integration. Further, the technique for circuit integration is not limited to LSI, and circuit integration may be implemented by using a dedicated circuit or a general-purpose processor. An FPGA (field-programmable gate array) that is programmable after manufacturing the LSI circuit, or a reconfigurable processor for which connections and settings of circuit cells within the LSI circuit can be reconfigured may be used.

In a case where a technique for circuit integration that replaces LSI emerges with the advancement of semiconductor technology or on the basis of technology that is separately derived, the functional blocks may be integrated by using the technique as a matter of course. For example, application of biotechnology is possible.

One aspect of the present disclosure need not be the detection device as described above and may be a detection method that includes characteristic constituent units included in the device as steps. Further, one aspect of the present disclosure may be a computer program for causing a computer to perform the characteristic steps included in the detection method. One aspect of the present disclosure may be a non-transitory computer-readable recording medium to which the computer program is recorded.

The present disclosure can be used as a detection device that detects a detection target substance in a sample with high accuracy on the basis of a change in the fluorescence lifetime of a fluorescent material.

What is claimed is:

1. A detection device for detecting a detection target substance using a metal material modified with a first substance having a property of specifically binding to the detection target substance and a fluorescent material modified with a second substance having a property of specifically binding to the detection target substance, the detection device comprising:
a light source configured to emit light for exciting the fluorescent material;
a photodetector configured to detect fluorescence emitted by the fluorescent material over time for a specific period from when emission of the light by the light source is stopped; and
a processor configured to:
(i) determine whether an intensity of the fluorescence detected by the photodetector is greater than or equal to a threshold intensity, wherein when it is determined that the intensity of the fluorescence is greater than or equal to the threshold intensity, the effect of fluorescence caused by nonspecific adsorption of the fluorescent material is configured to be reduced; and
(ii) detect the detection target substance found within a complex formed of the metal material, the detection target substance, and the fluorescent material modified with the second substance.

2. The detection device according to claim 1, wherein:
the processor is configured to detect the detection target substance found within the complex formed of the metal material, the detection target substance, and the fluorescent material modified with the second substance based on information which indicates whether a time, from when the light source stops emitting the light to when a ratio of the intensity of the fluorescence emitted by the fluorescent material to a maximum intensity of the fluorescence is equal to a specific ratio, is less than or equal to a threshold time.

3. The detection device according to claim 1, wherein;
the processor is configured to detect the detection target substance found within the complex formed of the metal material, the detection target substance, and the fluorescent material modified with the second substance based on information which indicates whether a ratio of an amount of attenuation of the intensity of the fluorescence to a maximum intensity of the fluorescence during a period from when the light source stops emitting the light to when a specific time elapses is greater than or equal to a threshold.

4. The detection device according to claim 1, wherein the metal material is in a form of particles.

5. The detection device according to claim 1, wherein the metal material is a metal microstructure on a substrate.

6. The detection device according to claim 1, wherein the metal material contains, as a main component, metal on which localized surface plasmon resonance corresponding to a frequency of the light emitted by the light source or a fluorescence frequency of the fluorescent material occurs.

7. A detection device comprising:
a light source configured to emit light to a sample liquid containing a fluorescent material modified with a second substance;
a photodetector configured to detect first and second intensities of fluorescence emitted by the fluorescent material excited by the light, for a specific period after emission of the light is stopped; and
a processor configured to:
(i) determine whether the first intensity is greater than or equal to a threshold intensity, wherein when it is determined that the first intensity is greater than or equal to the threshold intensity, the effect of fluorescence caused by nonspecific adsorption of the fluorescent material is configured to be reduced; and
(ii) determine whether the sample liquid contains a detection target substance based on the second intensity,
wherein the detection target substance directly binds to the second substance, and the detection target substance binds to a metal material with a first substance therebetween.

8. The detection device according to claim 7, wherein the processor is configured to determine whether the first intensity is greater than or equal to the threshold intensity, wherein when it is determined that the first intensity is greater than or equal to the threshold intensity, the effect of fluorescence emitted by the fluorescent material directly binding to the metal material is configured to be reduced.

9. The detection device according to claim 1, wherein the processor is configured to determine whether the intensity of the fluorescence detected by the photodetector is greater than or equal to the threshold intensity, wherein when it is determined that the intensity of the fluorescence is greater than or equal to the threshold intensity, the effect of fluorescence emitted by the fluorescent material directly binding to the metal material is configured to be reduced.

10. The detection device according to claim 4, wherein:
the metal material is neither directly nor indirectly fixed on a sensor cell which houses the detection target substance and the fluorescent material; and
the metal material is neither directly nor indirectly fixed on a substrate.

* * * * *